United States Patent
Chelur et al.

(10) Patent No.: US 9,382,574 B2
(45) Date of Patent: *Jul. 5, 2016

(54) DI- AND POLY-UBIQUITIN DEUBIQUITINASE SUBSTRATES AND USES THEREOF

(71) Applicants: Lifesensors, Inc., Malvern, PA (US); Progenra, Inc., Malvern, PA (US)

(72) Inventors: Dattananda Chelur, Chesterbrook, PA (US); Michael Eddins, West Chester, PA (US); Craig Leach, Ardmore, PA (US); Steven J. Orcutt, Audubon, PA (US); Raymond J. Peroutka, Baltimore, MD (US); James Strickler, Havertown, PA (US); Yilin Yan, Troy, NY (US); Kathryn Longenecker, West Chester, PA (US)

(73) Assignee: Lifesensors, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,941

(22) Filed: Aug. 26, 2013

(65) Prior Publication Data

US 2014/0072992 A1 Mar. 13, 2014

Related U.S. Application Data

(63) Continuation of application No. 13/168,073, filed on Jun. 24, 2011, now Pat. No. 8,518,660.

(60) Provisional application No. 61/358,177, filed on Jun. 24, 2010.

(51) Int. Cl.
  *C12Q 1/37* (2006.01)
  *C07K 14/00* (2006.01)
  *C12P 21/02* (2006.01)

(52) U.S. Cl.
  CPC . *C12Q 1/37* (2013.01); *C07K 14/00* (2013.01); *C12P 21/02* (2013.01)

(58) Field of Classification Search
  None
  See application file for complete search history.

(56) References Cited

U.S. PATENT DOCUMENTS

| 7,842,460 B2 | 11/2010 | Butt et al. |
| 2003/0104474 A1 | 6/2003 | Issakani et al. |
| 2004/0053324 A1 | 3/2004 | Wong et al. |

FOREIGN PATENT DOCUMENTS

EP         502448 A2 *  9/1992

OTHER PUBLICATIONS

Xu P et al. Characterization of Polyubiquitin Chain Structure by Middle-down Mass Spectrometry. 2008. Anal Chem. 80(9):3438-3444.*
Datta, A.B., et al. "The structure and conformation of Lys63-linked tetraubiquitin." J Mol Biol. Oct. 9, 2009;392 (5):1117-24. Epub Aug. 4, 2009.
Komander, D., et al. "Molecular discrimination of structurally equivalent Lys 63-linked and linear polyubiquitin chains." EMBO Rep. May 2009;10(5):466-73. Epub Apr. 17, 2009.
Cook, W.J., et al. "Structure of a diubiquitin conjugate and a model for interaction with ubiquitin conjugating enzyme (E2)." J Biol Chem. Aug. 15, 1992;267(23):16467-71.
Guraraja, T.L, et al. "A homogeneous FRET assay system for multiubiquitin chain assembly and disassembly." Methods Enzymol. 2005;399:663-82.
Pickart, C.M., et al. "Controlled synthesis of polyubiquitin chains." Methods Enzymol. 2005;399:21-36.
Eddins, M.J., et al. "Crystal structure and solution NMR studies of Lys48-linked tetraubiquitin at neutral pH." J Mol Biol. Mar. 16, 2007;367(1):204-11. Epub Dec. 29, 2006.
Gregori, L, et al. "A uniform isopeptide-linked multiubiquitin chain is sufficient to target substrate for degradation in ubiquitin-mediated proteolysis." J Biol Chem. May 25, 1990;265(15):8354-7.
BostonBiochem. "Continuous Fluorescent Diubiquitin Substrates: A New Substrate Discovery Platform." www.bostonbiochem.com. PH00001. Jan. 29, 2010;1-4.
BostonBiochem. Deconjugating Enzyme FRET Substrate Kit TAMRA/QXL Labeled Substrates Cat. #K-S16. Material Data Sheet. www.bostonbiochem.com. 2008;1-4.

* cited by examiner

*Primary Examiner* — Paul Holland
(74) *Attorney, Agent, or Firm* — Robert C. Netter, Jr.; Dann, Dorfman, Herrell & Skillman

(57) ABSTRACT

Methods for detection of the activity of proteolytic enzymes, particularly isopeptidases, are disclosed.

35 Claims, 8 Drawing Sheets

DI- AND POLY-UBIQUITIN DEUBIQUITINASE SUBSTRATES AND USES THEREOF

This application is a continuation application of U.S. patent application Ser. No. 13/168,073, filed on Jun. 24, 2011, now U.S. Pat. No. 8,518,660, which claims priority under 35 U.S.C. §119(e) to U.S. Provisional Patent Application No. 61/358,177, filed on Jun. 24, 2010. The foregoing applications are incorporated by reference herein.

FIELD OF THE INVENTION

The present invention relates to the field of detecting the activity of isopeptidases. More specifically, the present invention provides materials and methods for improved sensitivity in the fluorescent (e.g., internally quenched fluorescence technology) detection of isopeptidases such as deubiquitinating enzymes and other ubiquitin-like protein deconjugases by use of diubiquitin protein substrates.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

The study of ubiquitin pathway enzymes is hampered by the nature of ubiquitin modification. Ubiquitin (Ub) is transferred from a thioester linkage with the cysteine residue in the active site of a ubiquitin ligase (E2 or E3) to the ε-amine of a lysine residue in the target protein to form an isopeptide bond between the α-carboxyl of the C-terminal glycine of Ub and this amine. The requirement to form an isopeptide linkage places limits on the ability to mimic this process in vitro. Proteases, like most other enzymes, show a high degree of substrate specificity. This can range from relatively low stringency (requiring one of a few specific amino acids at the site of cleavage (the scissile bond)) to medium stringency (requiring a short, specific sequence surrounding the scissile bond) to high stringency (requiring recognition of structurally encoded sites on the target protein away from the scissile bond). This latter class can be exemplified by the ubiquitin and ubiquitin-like protein (UbL) deconjugating enzymes. These DUBs recognize both ubiquitin and the isopeptide bond which they cleave to release free Ub and the protein substrate. All currently available, high throughput compatible assays for DUB activity are based on the cleavage of a linear peptide- or amide-bond, while none measure true isopeptidase activity. In the past, linear peptide libraries have been used extensively to define the substrate specificity resulting from interactions between the side chains of residues surrounding the scissile bond and sub-sites within the active site of a protease for a wide variety of proteases including caspases, cathepsin S, and γ-secretase. The nature of the side chains and their interactions with the active site have been essential for guiding structure based drug design of small molecule inhibitors. These kinds of studies cannot be carried out with DUBs because linear peptides do not reflect the geometry of an isopeptide bond.

There are currently three commercially available assays for measuring the activity of Ub/Ub1 isopeptidases. The first assay consists of the Ub/Ub1 fused to a fluorophore, typically amino-methyl coumarin (AMC; FIG. 1A). Upon incubation with an isopeptidase, AMC is released and is associated with a detectable increase in fluorescence (Dang et al. (1998) Biochem., 37:4868-4879). The second assay is the Ubiquitin LanthaScreen™ reagent available from Invitrogen (Carlsbad, Calif.; U.S. Patent Application Publication No. 2007/0264678). This assay measures fluorescence resonance energy transfer between a fluorophore at the N-terminus of ubiquitin and a second fluorophore at the C-terminus. Incubation with an isopeptidase causes release of the fluorophore at the C-terminus of ubiquitin and a loss of fluorescence resonance energy transfer (FRET) signal. In addition to being a "loss of signal" readout, a major disadvantage of this assay format is the use of non-physiological substrates, given the observation that perturbations at the N-terminus of ubiquitin impact ubiquitin structure/function. The third assay is the CHOP reporter system (LifeSensors, Inc. (Malvern, Pa.); www.lifesensors.com; U.S. Patent Application Publication No. 2006/0040335). The substrate in this assay is an Ub-PLA$_2$ fusion from which an active PLA$_2$ enzyme is released upon incubation with an isopeptidase. Active PLA$_2$ cleaves a quenched fluorescent substrate causing an increase in fluorescence. This assay is extremely sensitive and works well with many members of the USP family, yet this assay still relies on cleavage of an amide bond within the substrate and is therefore not as physiologically relevant as diubiquitin.

While researchers wishing to measure Ub/Ub1 isopeptidase activity with a physiological substrate can obtain ubiquitin chains and detect the cleavage of these chains by SDS-PAGE followed by Western blotting with an antibody recognizing Ub/Ub1, this method is low throughput and time intensive. Moreover, kinetic parameters cannot be determined in such experiments.

Gururaja et al. have reported a fluorescence based homogeneous assay for monitoring multi-Ub chain assembly and disassembly (Gururaja et al. (2005) Methods Enzymol., 399: 663-682). The assay is based on the use of internally quenched fluorescent pairs. To add the quencher and fluorophore, the N-terminal methionine was changed to a cysteine. Additionally, a FLAG tag was added. Polymerization was carried out by using all the three enzymes (E1, E2 and E3) involved in conjugation and the quenching of fluorescence was monitored. Once the polyubiquitin was synthesized, the reaction was stopped and a DUB was added to monitor deubiquitylase activity. The assay had multiple components that required considerable standardization. Moreover, based on the crystal structure of ubiquitin, Vijay-Kumar et al. have proposed that the N-terminus of ubiquitin is virtually inaccessible (Vijay-Kumar et al. (1987) J. Mol. Biol., 194:531-544). Therefore, modification of the N-terminus interferes with the formation and recognition of diubiquitin. In fact, attaching a tag at the N-terminus of Ub has been known to interfere with the formation of K63-linked diubiquitins (Pickart et al. (2005) Methods Enzymol., 399:21-36). Development of this substrate requires multiple enzymes. Additionally, modifying the N-terminus of ubiquitin alters the structure of the protein and, thus, affect potential interactions with a DUB.

U.S. Patent Application Publication No. 2004/0053324 also describes the use of a FRET-based system to assay deubiquitinating activity. In a specific example of deubiquitinating activity, the FRET pair used is fluorescein and tetramethylaminorhodamine (TAMRA). As with Gururaja et al., the ubiquitin moiety is modified to have an N-terminal FLAG tag and an additional cysteine residue for linkage of the fluorescein. No other specific locations in the ubiquitin molecule for the placement of a fluorophore for the optimal assay of isopeptidase activity are described.

The mechanism by which certain Ub/Ub1-specific proteases recognize and cleave their cognate Ub/Ub1 substrate ("specificity") is not uniform. At the gene level, ubiquitin is encoded as a head-to-tail linked poly-ubiquitin (6-15 units of monomer Ub arranged in a head-to-tail fashion). Ubiquitin is also encoded as monomers linked to a C-terminal extension, such as a Ub-ribosomal fusion protein. In order for ubiquitin to enter the ubiquitinylation pathway and for conjugation of the C-terminus of ubiquitin to target proteins, linear poly-ubiquitin or ubiquitin carboxyl extension proteins must be cleaved by DUBs to form mature ubiquitins. Among the ~100 DUBs encoded by the human genome, selected DUBs are responsible for the generation of free ubiquitin to enter the ubiquitin pathway. Ubls, such as SUMO, are also encoded at the gene level in precursor form. Thus, nature has designed certain DUBs that recognize Ub and Ub1 C-terminal peptide extensions as substrates. In these cases, specificity is thought to be determined by discrete interactions between the protease and the amino acid residues in and around the active site. This assumption of specificity has led to the wide spread use of Ub/Ub1 conjugates that have a small adjunct (typically fluorescent in nature) linked to a C-terminus peptide. While these conjugates are cleaved to a measureable degree by some Ub/Ub1 specific proteases (such as UCHL3 (ubiquitin carboxyl-terminal hydrolase isozyme L3), SENP2 (sentrin-specific protease 2), PLpro (papain-like protease)), other Ub/Ub1-specific proteases exhibit no detectable activity towards these reporter molecules (such as Otubain2 (Otub2), AMSH (associated molecule with the SH3 domain of STAM), JosD1 (Josephin-1)). The activity of enzymes such as Otub2, AMSH, and JosD1 can be detected by the cumbersome and time consuming monitoring of polyubiquitin degradation by immunoblotting. Moreover, kinetic parameters cannot be determined from such assay formats. Presumably, the poor reactivity of Ub/Ub1 C-terminal adducts with certain proteases is related to specificity requirements beyond discrete interactions with amino acids surrounding the bond to be cleaved. Considering that the majority of known Ub/Ub1-specific proteases (100+) have not been adequately characterized with respect to relative activity or specificity, there exists a true need for novel reagents for the characterization of these isopeptidases. It is also desirable to provide an assay for isopeptidases that uses a physiologically relevant substrate and that generates a powerful signal of protease activity.

In view of the foregoing, there is a clear need for a better fluorescent method for detecting Ub isopeptidase activity using a physiologically relevant substrate which will also be useful in high-throughput screening (e.g., for drug discovery).

SUMMARY OF THE INVENTION

In accordance with the instant invention, diubiquitin substrates (as well as polyubiquitin substrates) are provided. The diubiquitins may be for measuring the isopeptidase activity of a deubiquitinase. In particular embodiments, the diubiquitin comprises a first ubiquitin molecule operably linked to at least one first energy transfer pair member and a second ubiquitin molecule operably linked at least one second energy transfer pair member, wherein said first ubiquitin molecule is operably linked to the second ubiquitin molecule by an isopeptide bond from the C-terminus of the first ubiquitin molecule to the side chain of a lysine residue of the second ubiquitin molecule. The first and second energy transfer pair members may individually either a fluorescent group or a quenching group. In certain embodiments, the first and second energy transfer pair members are attached to the first and second ubiquitin molecules at a cysteine residue. In still other embodiments, the cysteine residues are introduced at position 11, 20, 31, 34, 48, 57, or 63. Kits comprising at least one diubiquitin are also encompassed by the instant invention. Arrays/microarrays comprising at least one diubiquitin are also encompassed by the instant invention.

In accordance with another aspect of the instant invention, methods of synthesizing the diubiquitins are provided. The first and second ubiquitin molecules may be joined, e.g., by intein-based thioester chemistry or enzymatically with at least one enzyme. In certain embodiments, the enzymes include, without limitation, E1 ubiquitin activating enzyme, E2 ubiquitin conjugating enzyme, Ube1 ubiquitin activating enzyme, UBE2K ubiquitin conjugating enzyme, UBE2S ubiquitin conjugating enzyme, and Ubc13/MMS2 ubiquitin conjugating enzyme complex.

According to another aspect of the instant invention, methods for detecting an isopeptidase activity in a sample (e.g., a biological sample) are provided. In certain embodiments, the methods comprise contacting the sample with at least one diubiquitin of the instant invention and detecting fluorescence in the sample, wherein a change in the fluorescence is indicative of isopeptidase activity. In certain embodiments, the methods are performed in the presence and the absence of a test compound to screen for the compounds ability to modulate activity of at least one isopeptidase.

BRIEF DESCRIPTION OF THE DRAWINGS

FIG. 4 presents graphs demonstrating the increase in fluorescence upon cleavage of K48 linked IQF-diubiquitin Q63T11 (DiUb48-5) by USP2core.

DETAILED DESCRIPTION OF THE INVENTION

Figure 1:
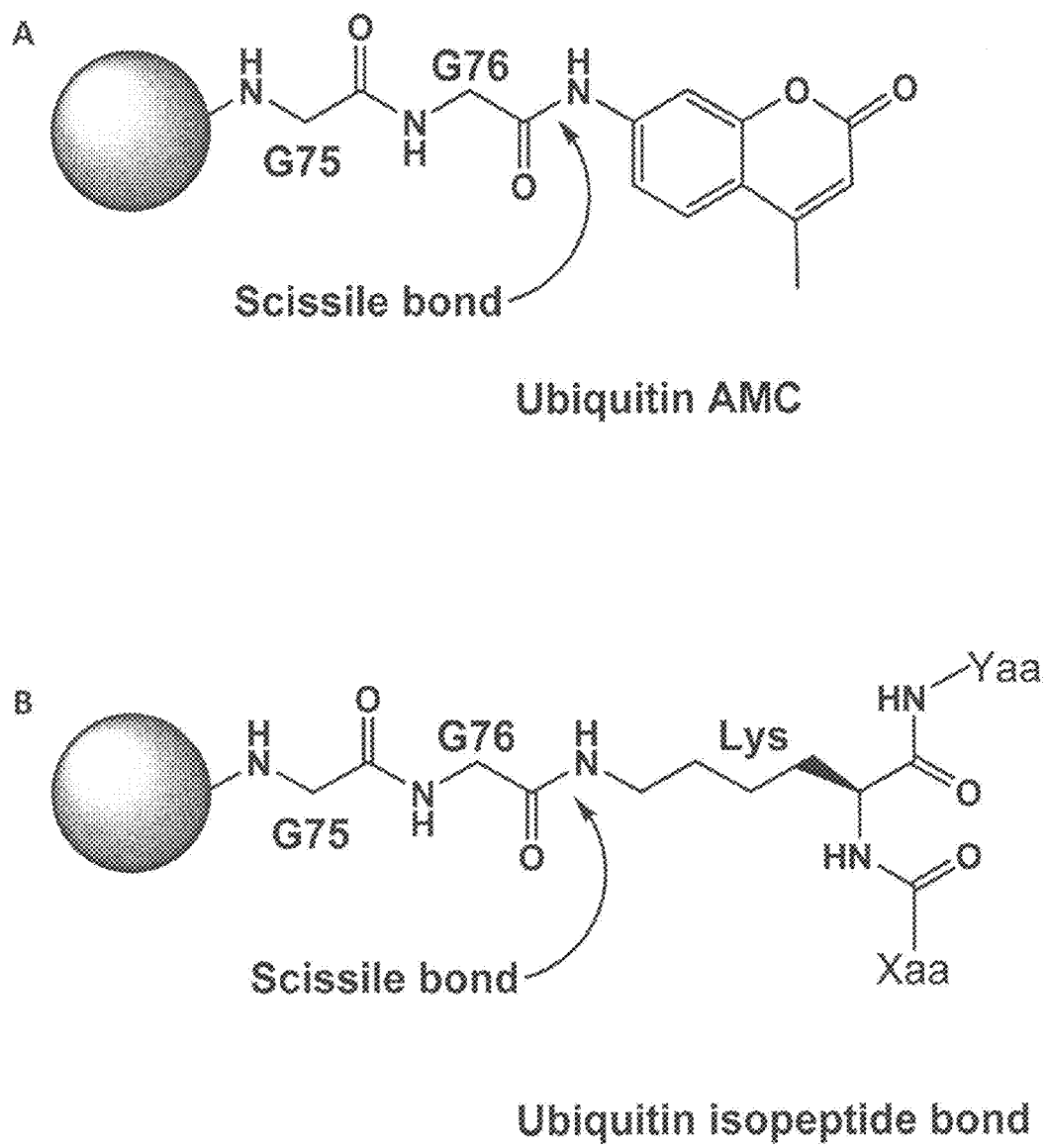
FIG. 1A provides a schematic representation of Ubiquitin AMC with an amide bond.
FIG. 1B provides a schematic representation of a ubiquitin linked to the lysine residue of a protein via an isopeptide bond, wherein Yaa and Xaa each represent at least one amino acid.
Figure 2:
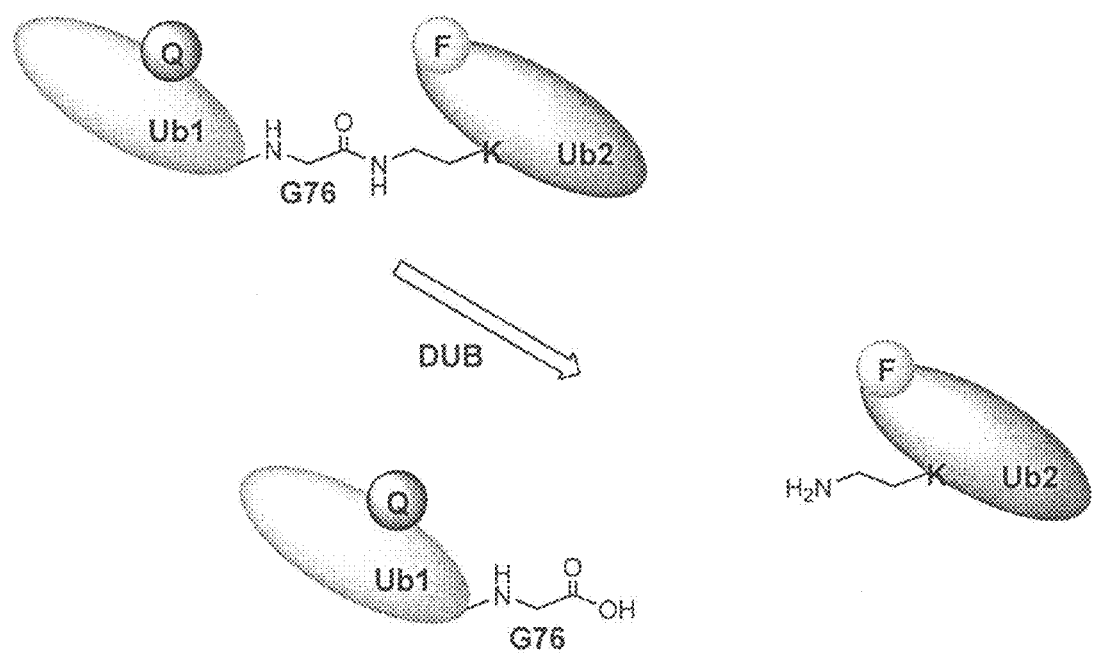
FIG. 2 presents a schematic of the isopeptidase cleavage of a diubiquitin substrate, wherein Q represents a quencher and F represents a fluorescent molecule. The distal ubiquitin is labeled Ub1 while the proximal ubiquitin is labeled Ub2.

The present invention provides methods and corresponding reagents for improved methods for fluorescent detection of isopeptidase activity. The methods and corresponding reagents are based, in part, on the use of physiologically relevant isopeptidase substrates for the detection and measurement of the activity of deubiquitinating enzymes (DUBs). In particular embodiments, the isopeptidase substrate is a diubiquitin substrate labeled with an internally-quenched energy transfer pair. In a particular embodiment, one ubiquitin of the diubiquitin is labeled with at least one first energy transfer pair member and the second ubiquitin of the diubiquitin is labeled with at least one second energy transfer pair member. For example, one ubiquitin may be labeled with a fluorescent group and the other ubiquitin may be labeled with an appropriate/corresponding quenching member. The two ubiquitin molecules of the diubiquitin are linked to each other via an isopeptide bond between the C-terminus of one of the ubiquitin molecules and the epsilon-amino group on the side chain of a lysine residue on the other ubiquitin molecule (see, e.g., FIG. 1B). Fluorescence is quenched while the two ubiquitin molecules are linked as a diubiquitin. However, upon action of an isopeptidase, the isopeptide linkage is cleaved and the two ubiquitin molecules and associated fluorophore labels are separated, whereby a fluorescent signal is emitted (see, FIG. 2).

As stated hereinabove, the isopeptidase substrates of the present invention utilize internally quenched fluorescence (IQF) based Förster resonance energy transfer (a.k.a. fluorescence resonance energy transfer; FRET) technology to produce a gain-of-signal readout to detect or measure/quantify isopeptide bond cleavage by an enzyme (e.g., a deubiquitinase). In the substrates of the invention, an isopeptide bond is formed between the C-terminus of one ubiquitin molecule (the distal ubiquitin) and the ϵ-amino group on the side chain of a lysine residue of the second ubiquitin molecule (the proximal ubiquitin). The two ubiquitin molecules can be joined either chemically (e.g., using intein based thioester methodology) or enzymatically (e.g., using recombinant ubiquitin E2 conjugating enzymes). The term "proximal ubiquitin" is used to denote the ubiquitin that would be attached to a target protein in vivo, while the term "distal ubiquitin" refers to the ubiquitin or ubiquitins that would be attached to the proximal ubiquitin in a polyubiquitin chain.

To form the IQF substrate of the instant invention, each of the ubiquitin molecules in the diubiquitin is attached to at least one energy transfer pair member so as to form an energy transfer pair. In particular embodiments, one of the two ubiquitin molecules in the diubiquitin is labeled with a fluorescent group and the second ubiquitin molecule is labeled with a matching/corresponding quenching group. In particular embodiments, the fluorescent group is attached to the distal ubiquitin and the quencher group is attached to the proximal ubiquitin. In other embodiments, the fluorescent group is attached to the proximal ubiquitin and the quencher group is attached to the distal ubiquitin. Each monomer of ubiquitin may be labeled with the dye molecule prior to the conjugation reaction to generate the diubiquitin. The ubiquitin monomers may have the energy transfer pair member attached at a single, specific site. In some embodiments, this is achieved by mutation of a single residue in the ubiquitin molecule to a different and, optionally, unique residue that has a chemically reactive side chain (e.g., a cysteine residue). In yet another embodiment, a cysteine residue or other (optionally) unique residue having a chemically reactive side chain can be can be inserted into the Ub sequence. The energy transfer pair member is then reacted with the target amino acid. For example, the energy transfer pair member may be reacted with the side chain thiol of the cysteine residue using thiol specific chemistry (e.g., by using iodoacetamide, maleimide, aziridine, etc.). In yet another embodiment, energy transfer pair members can be attached by "click" chemistry (see, for example, Best, M. D. (2009) Biochem., 48:6571-6584). For example, a non-natural amino acid may be introduced at any position, particularly between residues 8 and 70, by site-specific mutagenesis and the use of modified tRNA/amino acyl tRNA pairs (see, e.g., Best, M. D. (2009) Biochem., 48:6571-6584) and the energy transfer pair member may be added thereto.

The placement of individual energy transfer pair members on each ubiquitin molecule is important for maintaining recognition of the diubiquitin by enzymes (e.g., DUBs). Moreover, it is important to select appropriate energy transfer pairs based on the distance between the energy transfer pair members to ensure proper quenching. Indeed, FRET (e.g., IQF-FRET) efficiency is dependent on the distance between the donor and the acceptor (fluorescent group and quencher group, respectively) and decreases with the square of the distance between the pair. For example, quenching often occurs when the energy transfer pair members are within about 10 to 100 angstroms. Furthermore, as stated above, the site of modification can interfere with recognition of the substrate by the deubiquitinase. Accordingly, a series of diubiquitins may be prepared with the energy transfer pair members in different positions in order to allow optimization of a given diubiquitin substrate for an individual DUB. Labeling with an energy transfer pair member could also interfere with conjugation (particularly enzymatically). Therefore, a series of labeled ubiquitins may be prepared in order to ensure the ability to efficiently generate the diubiquitin molecules after labeling. These factors affect the functionality for each diubiquitin IQF substrate as well as the commercial viability of the product. Finally, with regard to the sites of modification, it is also important that the mutation of any given residue within ubiquitin, or the introduction of any residue, not have a significant adverse affect on either the overall structure or the local structure of the ubiquitin molecule, i.e., the native structure of the ubiquitin molecule should be maintained to the highest extent possible. For this reason, mutations affecting the N- or C-termini of the molecule have been avoided.

Methods of the present invention are amenable to high-throughput screening (HTS) formats, since the use of fluorescence and FRET based assays is a standard platform known in the art for HTS.

According to another aspect of the instant invention, the diubiquitins of the instant invention may be contained within a microarray (e.g., in a microassay plate). The microarrays may comprise at least one, at least 5, at least 10, at least 25, at least 50, at least 75, at least 96, or more different diubiquitins. Such microarrays allow for researchers to quickly and cost effectively ascertain which specific diubiquitin IQF substrate is ideal for the DUB tested. For example, one or more DUBs would be added to each sample of the microarray at desired concentrations in appropriate reaction buffer prior to monitoring for gain of fluorescence.

Ubiquitin Molecules

Ubiquitin (Ub) proteins are well known in the art. In particular embodiments, full-length Ub is used in the diubiquitins of the instant invention. In other embodiments, a fragment of Ub is used in the diubiquitins of the instant invention. The Ub fragments are active as substrates for isopeptidases. In particular embodiments, the Ub fragment comprises at least 25%, 30%, 40%, 50%, 60%, 70%, 75%, 80%, 85%, or, more particularly, 90%, 95%, 97%, 99% or more of the full-length Ub, wherein the fragment comprises the C-terminus.

As stated above, the Ub moieties of the isopeptidase substrates of the instant invention may comprise a full-length (e.g., 76 amino acids) ubiquitin protein. An exemplary amino acid sequence of ubiquitin is the mature human ubiquitin:

```
                                            (SEQ ID NO: 1)
    MQIFVKTLTG KTITLEVEPS DTIENVKAKI QDKEGIPPDQ

QRLIFAGKQL EDGRTLSDYN IQKESTLHLV LRLRGG,
``` which is derived by post-translational processing of the naturally occurring human ubiquitin precursor, disclosed at GenBank Accession No CAA44911 (Lund et al., 1985, J. Biol. Chem., 260:7609-7613).

Ubs suitable for the methods and substrates of the present invention can come from any species including, without limitation, human and yeast. Any ubiquitin can be used in the substrates and methods of the present invention for detecting activity of a cognate isopeptidase. In particular embodiments, the Ub moieties of the diubiquitin are the mature form of the protein, i.e., the form of the protein after the precursor has been processed by a hydrolase or peptidase. In particular embodiments, the Ub is a mammalian ubiquitin, more particularly, a human ubiquitin.

Recombinant engineering and expression methods are well known to the art and are described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.

The Ub molecules of the isopeptidase substrates of the present invention may comprise at least one mutation (e.g., at least 1, 2, 3, 4, 5, or more mutations or insertions) from the wild-type amino acid sequences for Ub. In particular embodiments, the ubiquitin molecule has at least 75%, 80%, 85%, or more particularly, at least 90%, 95%, 97%, or 99% homology with SEQ ID NO: 1. Each of the ubiquitin molecules of the diubiquitin may be mutated in the same way or mutated differently. In some embodiments, the Ub moiety has at least one (e.g., only one) cysteine residue introduced by substitution or insertion into the sequence for the attachment of an energy transfer pair member. In particular embodiments, at least one amino acid in the region of amino acid residues 8 through 70 of SEQ ID NO: 1 is substituted for a cysteine residue or at least one cysteine residue is inserted in the region of amino acid residues 8 through 70 of SEQ ID NO: 1. In still further embodiments, a cysteine residue replaces at least one of the amino acid residues at position 11, 20, 31, 34, 48, 57, or 63 of SEQ ID NO: 1. In still other embodiments, one or more of the lysine residues in the Ub protein are mutated (e.g., changed to another amino acid). For example, one or more of the Ub lysine residues at amino acid position 6, 11, 27, 29, 33, 48, and 63 of SEQ ID NO: 1 are changed to another amino acid. In particular embodiments, the Ub moieties do not contain an N-terminal tag.

Those of skill in the art are aware of methods for determining sequence identity. Calculation of sequence identity can, for example, be performed by published algorithms. Alignment of sequences for comparison may be conducted by the local homology algorithm of Smith & Waterman, 1981, Adv. Appl. Math., 2:482, by the homology alignment algorithm of Needleman & Wunsch, 1970, J. Mol. Biol., 48:443, by the search for similarity method of Pearson & Lipman, 1988, Proc. Natl. Acad. Sci. U.S.A., 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

Any variant Ub protein is contemplated for use in the substrates and methods of the invention, with the proviso that the variant remains active for cleavage from the diubiquitin structure by an isopeptidase. Variant Ub proteins include those having one or more amino acid substitutions, deletions or insertions in comparison to the wild-type Ub. In particular embodiments, a Ub protein will have one or more amino acid substitutions, deletions or insertions that can be conservative or non-conservative. As used herein, a "conservative" amino acid substitution/mutation refers to substituting a particular amino acid with an amino acid having a side chain of similar nature (i.e., replacing one amino acid with another amino acid belonging to the same group). A "non-conservative" amino acid substitution/mutation refers to replacing a particular amino acid with another amino acid having a side chain of different nature (i.e., replacing one amino acid with another amino acid belonging to a different group). Groups of amino acids having a side chain of similar nature are known in the art and include, without limitation, basic amino acids (e.g., lysine, arginine, histidine); acidic amino acids (e.g., aspartic acid, glutamic acid); neutral amino acids (e.g., glycine, asparagine, glutamine, serine, threonine, tyrosine, cysteine, alanine, valine, leucine, isoleucine, proline, phenylalanine, methionine, tryptophan); amino acids having a polar side chain (e.g., glycine, asparagine, glutamine, serine, threonine, tyrosine, cysteine); amino acids having a non-polar side chain (e.g., alanine, valine, leucine, isoleucine, proline, phenylalanine, methionine, tryptophan); amino acids having an aromatic side chain (e.g., phenylalanine, tryptophan, histidine); amino acids having a side chain containing a hydroxyl group (e.g., serine, threonine, tyrosine), and the like.

In particular embodiments, the distal ubiquitin comprises mutations at amino acid positions 11, 29, 48, and 63 (with reference to SEQ ID NO: 1). In still other embodiments, the distal ubiquitin comprises mutations at amino acid positions 48 and 63 (with reference to SEQ ID NO: 1). Mutations of the lysines at positions 48 and 63 are incorporated to prevent oligomerization of the ubiquitins during enzymatic conjugation. In a particular embodiment, the mutations of the lysines at positions 48 and 63 are conservative (e.g., to arginine) or non-conservative (e.g., to cysteine). In particular embodiments, at least one residue of SEQ ID NO: 1 is changed to a cysteine or a cysteine is added. In yet another embodiment, when the lysines at positions 48 and 63 are changed to an amino acid other than cysteine, then at least one other amino acid is changed to a cysteine or a cysteine is added to the sequence. In a particular embodiment, the distal ubiquitin comprises the following amino acid mutations (amino acid positions are relative to SEQ ID NO: 1):

1) K48 to R, K63 to R, and K11 to C;
2) K48 to C and K63 to R;
3) K48 to R and K63 to C; or
4) K48 to R, K63 to R, and S57 to C.

In other embodiments, the proximal ubiquitin comprises mutations (conservative, non-conservative, or deletion) to the two terminal glycines (positions 75 and 76). Mutation of the two C-terminal glycines prevents formation of diubiquitin molecules exclusively from the proximal monomer. In a particular embodiment, the glycines are changed to alanines. At least one residue of SEQ ID NO: 1 may be changed to a cysteine or a cysteine is added. In a particular embodiment, at least one of K11, S20, Q31, and E34 (particularly K11 or S20) is changed to a cysteine. In still another embodiment, the proximal ubiquitin comprises the following amino acid mutations (amino acid positions are relative to SEQ ID NO: 1):
  1) K11 to C and G75 and G76 to A, or
  2) S20 to C and G75 and G76 to A.

In a particular embodiment, the proximal ubiquitins may further comprise a separate fluorophore at its C-terminus (i.e., not part of the energy transfer pair). Intein chemistry may be used to add the fluorophore to the C-terminus. The fluorophore may be separate and non-overlapping with the energy transfer pair used in the diubiquitin. In a particular embodiment, the fluorophore is aminomethyl coumarin (AMC). This allows monitoring of both isopeptidase and C-terminal hydrolase activities simultaneously with a single substrate. In addition, such a construct allows for monitoring C-terminal hydrolases that require a minimum of a diubiquitin moiety for activity. Incorporation of alanine residues and intein chemistry at the C-terminus of the distal ubiquitin allows for the formation of non-hydrolysable isopeptide bonds to investigate C-terminal hydrolases that require a minimum of a diubiquitin moiety for activity. These latter diubiquitins may be synthesized chemically rather than enzymatically.

The ubiquitin monomers may be linked via any isopeptide bond. In particular embodiments, the monomers are linked via any lysine (e.g., a lysine native to the ubiquitin or a lysine added to the ubiquitin sequence). In particular embodiments, the monomers are linked via at least one of position 6, 11, 27, 29, 33, 48, or 63, particularly positions 48 or 63. Diubiquitins may be synthesized enzymatically using specific E2 conjugating enzymes. For example, UBE2K (a.k.a. E2-25K) has been used for K48 linked diubiquitins and yeast Ubc13/MMS2 has been used for K63 linked diubiquitins. Table 1 provides examples of E2 conjugating enzymes. Diubiquitins may be also synthesized chemically (e.g., by intein chemistry).

TABLE 1

Examples of E2 enzymes.

| Name | Alternate names | Accession No. |
|---|---|---|
| UBE2K | Ubc1, HIP-2, E2-25K | P61086 |
| UBE2B | HR6B, RAD6B, hUbc2b | P63146 |
| UBE2G2 | Ubc7 | P60604 |
| UBE2R1 | Cdc34, Ubc3, E2-32K | P49427 |
| UBE2R2 | Cdc34b, Ubc3B | Q712K3 |
| UBE2D1 | UbcH5A, E2-17k1 | P51668 |
| UBE2D2 | UbcH5B, UBC4, E2-17K2 | P62837 |
| UBE2D3 | UbcH5C, E2-17K3 | P61077 |
| UBE2D4 | HBUCE1 | Q9Y2X8 |
| UBE2E2 | | Q96LR5 |
| UBE2E3 | UBCE4, UbcH9, UbcM2, E2-23K | Q969T4 |
| UBE2J2 | NCUBE2 | Q8N2K1 |
| UBE2H | UbcH2, E2-20K | P62258 |
| UBE2I | Ubc9 | P63279 |
| UBE2F | NCE2 | Q969M7 |
| UBE2M | Ubc12 | P61081 |
| UBE2N | Ubc13, BLU | P61088 |
| UBE2T | HSPC150 | Q9NPD8 |
| UBE2V2 | MMS2, EDPF-1, UEV2 | Q15879 |
| UBE2S | E2-EPF5, E2-24K, EPF | Q16763 |
| UBE2C | UBCX, UbcH10 | O00762 |
| UBE2W | | Q96B02 |
| UBE2Z | Use1, HOYS7 | Q9H832 |
| UBE2L3 | UbcH7, E2-F1, L-UBC, UBCE7 | P68036 |
| UBE2L6 | UbcH8, RIG-B | O14933 |
| AKTIP | FTS | Q9H8T0 |
| UBE2Q2 | | Q8WVN8 |

While the isopeptidase substrates of the instant invention are described herein as diubiquitins, the instant invention also encompasses poly ubiquitins or ubiquitin chains comprising the diubiquitin molecules of the instant invention. For example, at least one, two, three, four, five, or more ubiquitins may be added to the diubiquitin molecules of the instant invention (e.g., on the distal ubiquitin of the instant invention). The additional ubiquitins may be wild-type (i.e., not modified as described hereinabove for the ubiquitin monomers of the diubiquitin) or modified ubiquitins as described hereinabove.

While the isopeptidase substrates of the instant invention are described herein as diubiquitins, the instant invention also encompasses poly- and di-ubiquitin-like proteins (di-Ubls). In a particular embodiment, the Ubl of the di-Ubl is the mature form of the protein, i.e., the form of the protein after the precursor has been processed by a hydrolase or peptidase. In particular embodiments, the Ubl is a mammalian Ubl, more particularly, a human Ubl. Ubls include, without limitation, small ubiquitin like-modifier-1 (SUMO), SUMO-2, SUMO-3, SUMO-4, ISG-15, HUB1 (homologous to ubiquitin 1; also known as UBL5 (ubiquitin-like 5)), APG12 (autophagy-defective 12), URM1 (ubiquitin-related modifier 1), NEDD8 (RUB1), FAT10 (also known as ubiquitin D), and APG8 Amino acid sequences of Ubls and nucleic acid sequences encoding Ubls are known in the art. Amino acid and nucleotide sequences of SUMO proteins are provided, for example, in U.S. Pat. No. 7,060,461 and at GenBank Accession Nos. Q12306 (SMT3; amino acids 1-98 is the mature form), P63165 (SUMO1; precursor shown, mature form ends in GG), NM_001005781.1 (SUMO1; precursor shown, mature form ends in GG), NP_003343.1 (SUMO1; precursor shown, mature form ends in GG), NM_006937.3 (SUMO2; precursor shown, mature form ends in GG), NM_001005849.1 (SUMO2; precursor shown, mature form ends in GG), NM_006936.2 (SUMO3; precursor shown, mature form ends in GG), and NM_001002255.1 (SUMO4; precursor shown, mature form ends in GG). GenBank Accession No. CAI13493 provides an amino acid sequence for URM1. GenBank Accession No. NP_001041706 provides an amino acid sequence for UBL5 (aka HUB 1) (amino acids 1-72 represent the mature form). GenBank GeneID No. 4738 and GenBank Accession No. NP_006147 provide amino acid and nucleotide sequences of NEDD8 (RUB1) (precursor shown, mature form ends in LRGG). GenBank Accession No. P38182 provides an amino acid sequence of yeast ATG8 (aka APG8) (precursor shown, mature form ends in FG). GenBank Accession Nos. BAA36493 and P38316 provide amino acid sequences of human and yeast ATG12 (aka APG12), respectively (human precursor shown, mature form ends in FG). GenBank Accession Nos. AAH09507 and P05161 provide amino acid sequences of human and yeast ISG15 ubiquitin-like modifier, respectively (precursors shown, mature form ends in GG). GenBank Accession No. AAD52982 provides an amino acid sequence of ubiquitin D (aka human FAT10, UBD-3, UBD, GABBR1). Corresponding mutations made to ubiquitin, as described hereinabove, would be made to the Ubls.

Energy Transfer Pair Members

Any energy transfer pair can be used with the substrates and methods of the invention. Energy transfer pairs include, without limitation, (fluorescent group (donor)-quencher group (acceptor)):
  tetramethylaminorhodamine (TAMRA)-QXL™ 570 (AnaSpec, Inc., Fremont, Calif.);
  4-[{4-(dimethylamino)phenyl}azo]benzoic acid (DABCYL)-5-[(2-aminoethyl)amino]naphthalene-1-sulfonic acid (EDANS);
  fluorescein—TAMRA;
  fluorescein—QXL™ 490 (AnaSpec, Inc.);

fluorescein—TIDE Quencher™ 2 (AAT Bioquest, Inc.; Sunnyvale, Calif.);

5-({2-[(iodoacetyl)amino]ethyl}amino)naphthalene-1-sulfonic acid (IAEDANS)—fluorescein isothiocyanate (FITC);

IAEDANS-5-(iodoacetamide)-fluorescein;

Alexa Fluor® 488 (Invitrogen)-tetramethylrhodamine fluorescein—fluorescein;

EDANS—DABCYL;

tryptophan—IAEDANS;

tryptophan—dansyl;

tryptophan—pyrene;

dansyl—fluorescein;

naphthalene—dansyl;

pyrene—coumarin;

B-Phycoerythrin—Cys5;

TAMRA—Black Hole Quencher™ 2 (BHQ™ 2; Biosearch Technologies; Novato, Calif.).

In particular embodiments, the TAMRA/QXL™ 570 pair of labels is used. Other fluorphores include, without limitation, 5-FAM (5-Carboxyfluorescein), tetrachloro-6-carboxyfluorescein (TET), 2,7-dimethoxy-4,5-dichloro-6-carboxyfluoroscein (JOE), hexachlorofluorescein (HEX), Oregon Green®, Alexa Fluor®, ROX, Cy3, Cy3.5, CAL Red™, Red 640, Cy5, and Cy5.5. Other quenchers include, without limitation, any other QXL™ or BHQ™ quencher.

Isopeptidases

Methods and substrates of the present invention can be used to detect/measure the activity or presence of a wide variety of enzymes, particularly isopeptidases, from any organism. More than one isopeptidase substrate may be used for isopeptidase activity detection. Isopeptidases include deubiquitinating enzymes and ubiquitin-like protein (Ubl)-specific proteases (Ulp). In a particular embodiment, the isopeptidase is a deubiquitinase. Examples of isopeptidases include, without limitation: ULP1, ULP2, SENP1, SENP2, SENP3, SENP5, SENP6 (aka SUSP1, SSP1), SENP7, NEDD8-specific protease 1 (aka DEN1, Nedp1, Prsc2, SENP8), yeast YUH1, mammalian UCH-L1 (aka Park 5), UCH-L3, UCH-L5 (aka UCH37), USP1 (aka UBP), USP2 (aka UBP41), USP2core, USP2a, USP2b, USP3, USP4 (aka UNP, UNPH), USP5 (aka isopeptidase T, ISOT), USP6 (aka TRE2, HRP-1), USP7 (aka HAUSP), USP8 (aka UBPY), USP9, USP9Y (aka DFFRY), USP9X (aka DFFRX), USP10 (aka UBPO, KIAA0190), USP11 (aka UHX1), USP12 (aka USP12L1, UBH1), USP13 (aka ISOT3), USP14 (aka TGT), USP15, USP16 (aka UBP-M), USP18 (aka UBP43, ISG43), USP19 (aka ZMYND9), USP20 (aka VDU1, LSFR3A), USP21, USP22 (aka KIAA1063), USP23, USP24, USP25, USP26, USP27, USP28, USP29, USP30, USP32, USP33 (aka VDU2), USP34, USP35, USP36, USP37, USP38, USP40, USP42, USP44, USP46, USP49, USP51, JosD1 (aka KIAA0063), JosD2 (aka RGD1307305), AMSH, AMSH-core, Ataxin3 (aka ATX3, MJD, MJD1, SCA3, ATXN3), Ataxin3-like, Bap1 (UCHL2 or HUCEP-13), DUB-1, DUB-2, DUB1, DUB2, DUB3, DUB4, CYLD, CYLD1, FAFX, FAFY, OTUB1 (aka OTB1, OTU1, HSPC263), OTUB2 (aka OTB2, OTU2, C14orf137), OUT domain containing 7B (aka OTUD7B, Cezanne), KIAA0797, KIAA1707, KIAA0849, KIAA1850, KIAA1850, KIAA0529, KIAA1891, KIAA0055, KIAA1057, KIAA1097, KIAA1372, KIAA1594, KIAA0891, KIAA1453, KIAA1003, UBP1, UBP2, UBP3, UBP4, UBP5, UBP6, UBP7, UBP8, UBP41, UBP43, VCIP135, Tnfaip3 (aka A20), PSMD14 (aka POH1), COPS complex homolog subunit 5 (aka CSN5, COPS5, JAB1) YPEL2 (aka FKSG4, and SARS CoV PLpro. Isopeptidases and their nucleic acid coding sequences are well known to those of skill in the art. For use in certain embodiments, isopeptidases can be isolated or recombinantly produced by methods well known in the art. In particular embodiments, the methods and substrates of the present invention are used to detect the activity or presence of an isopeptidase selected from USP2core, USP7, USP8, USP34, Otub2, JosD1, JosD2, AMSH, Ataxin3, Ataxin3-like, USP20, USP14, A20 and SENP5.

In some embodiments, methods of the present invention are practiced using a sample in which the activity of an isopeptidase will be detected. Samples may be from a variety of sources including animal or plant cell or cellular lysates, in vitro reaction mixtures, such as for drug screening purposes, including solutions and/or mixtures containing recombinantly produced isopeptidase, and bodily fluids or tissue samples taken from an animal such as a human (e.g., biological samples).

Methods for Screening for Agents that Modulate Isopeptidase Activity

The present invention also provides methods for screening for agents that can modulate the activity of a particular isopeptidase of interest. In these methods, an appropriate isopeptidase substrate of the invention will be contacted with an isopeptidase in the presence and in the absence of one or more test agents. This contacting will take place under appropriate conditions for the isopeptidase to cleave the isopeptidase substrate, thereby separating the quenched energy transfer pairs (FRET pairs), which will generate a fluorescent signal that can be detected and quantified. Any alteration or difference in the level of fluorescence detected in the presence of the one or more test agent, as compared with the level of fluorescence detected in the absence of the one or more test agent, will be an indication that the one or more test agent is capable of modulating the activity of the isopeptidase.

As used herein, "modulate" and "capable of modulating", in reference to a test agent or agent, includes agents that can increase/enhance or inhibit/decrease/diminish the activity of a particular isopeptidase. Therefore, screening methods of the present invention are useful for identifying agents that can increase/enhance or inhibit/decrease/diminish the activity of a particular isopeptidase.

Any kind of compound or molecule may be tested as a candidate isopeptidase modulating agent in the methods of the present invention, including, but not limited to, natural or synthetic chemical compounds (such as small molecule compounds (including combinatorial chemistry libraries of such compounds)), extracts (such as plant-, fungal-, prokaryotic- or animal-based extracts), fermentation broths, organic and inorganic compounds and molecules, and biological macromolecules (such as saccharide-, lipid-, peptide-, polypeptide- and nucleic acid-based compounds and molecules). The activity of a modulator may be known, unknown, or partially known.

Candidate isopeptidase modulating agents may be evaluated for potential activity as inhibitors or enhancers (directly or indirectly) of a biological process or processes associated with a particular isopeptidase, such as for example, a particular Ub- or Ubl-specific isopeptidase (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening methods and assays described herein.

Agents identified as capable of modulating the activity of particular isopeptidases using the methods of the present invention may useful for the preparation of drugs for the treatment of diseases or conditions associated with a particular isopeptidase, such as a Ub- or Ub1-specific isopeptidase or its corresponding Ub or Ub1, as well as for further dissecting the mechanisms of action of these enzymes.

Method for Diagnosing Diseases Associated with Isopeptidase

The present invention also provides methods for diagnosing a disease or condition associated with a particular Ub- or Ub1-specific isopeptidase, where a sample from a subject suspected of having the disease or condition is contacted with an appropriate isopeptidase substrate of the present invention, followed by detection of fluorescence. The level of fluorescence is indicative of the isopeptidase activity in the sample. The amount of isopeptidase activity in the sample can be compared to the amount of isopeptidase activity in a corresponding sample from a healthy control, wherein a modulation (e.g., increase or decrease) in the isopeptidase activity in the sample compared to healthy controls is indicative of the presence of a disease or disorder.

Many diseases or conditions are known to be associated with an isopeptidase, such as for example, a Ub- or Ub1-specific proteolytic enzyme. For example, diseases or conditions associated with a Ub- or Ub1-specific proteolytic enzyme may be associated with altered enzyme levels, amounts, sequences and/or activities. Particular diseases or conditions associated with a Ub- or Ub1-specific proteolytic enzyme include, but are not limited to, auto-immune, neoplastic, metabolic, vascular, neurodegenerative and other genetic diseases or conditions.

Methods of the present invention can be used to diagnose diseases or conditions in subjects of any organism, plant or animal, suspected of having a disease or condition associated with a particular Ub- or Ub1-specific proteolytic enzyme. Therefore, the sample from the subject may include a cell or cells, a piece of tissue, cellular or tissue extract, or bodily fluid from such organism. In particular embodiments, the sample is from a human patient suspected of having a disease or condition associated with a particular Ub- or Ub1-specific proteolytic enzyme.

Any disease or condition known to be associated with a Ub- or Ub1-specific proteolytic enzyme can be detected using the methods of the present invention. Specific examples of the diseases or conditions associated with a Ub- or Ub1-specific proteolytic enzyme are cancer, e.g., breast, prostate, and cancers associated with von Hippel-Lindau disease which predisposes to a number of cancers such as hemangioblastomas, pheochromocytomas, and cystadenomas, as well as other diseases such as lupus, diabetes, IBD, Parkinson's disease and cardiovascular disease. Examples of proteolytic enzyme/isopeptidase/deubiquitinating enzymes associated with disease include the following.

VDU1/2 and Cancer von Hippel-Lindau disease is an hereditary cancer syndrome caused by germline mutations of the VHL gene (Sims, 2001, Curr. Opin. Neurol., 14:695-703). von Hippel-Lindau predisposes those with the disease to various tumors, including hemangioblastomas in the CNS and retina, clear cell renal carcinomas, pheochromocytomas of adrenals, pancreatic tumors, cystadenomas of the epididymis, and tumors of the inner ear (Li et al., 2002, J. Biol. Chem. 277:4656-62; Maher, et al., 1997, Medicine (Baltimore), 76:381-91). VHL protein (pVHL) associates with elongin C, elongin B, and cullin-2 to form a complex, VCB-CUL2, which acts as an ubiquitin E3 ligase (Lisztwan et al., 1999, Genes Dev., 13:1822-1833). Because mutated pVHL is associated with malignancies, the ligase can be considered to be a tumor suppressor and its substrates potential oncogenic molecules. Hypoxia-inducible factor (HIF-α), known to be a substrate of VCB-CUL2, plays a role in development of hemangioblastomas, and likely in tumor angiogenesis in general, via VEGF induction (Ohh et al., 2000, Nat. Cell Biol., 2(7):423-427; Tyers et al., 1999, Proc. Natl. Acad. Sci. USA, 96(22):12230-12232; Benjamin et al., 1997, Proc. Natl. Acad. Sci. USA, 94(16):8761-8766). Also among its substrates, is ubiquitin isopeptidase USP20 (aka VDU1), found by yeast 2-hybrid screening to interact with pVHL. A highly homologous protease, USP33 (aka VDU2), is also known; although it has not been studied in terms of pVHL association, VDU2 has physiological substrates in common with VDU1 (Curcio-Morelli et al., 2003, J. Clin. Invest., 112(2):189-196). The β-domain region of pVHL, a site of naturally occurring mutations, is the locus of VDU1 interaction, and VDU1 may be co-immunoprecipitated in the VCB-CUL2 complex. The ubiquitination and degradation of VDU1 by a pVHL-dependent pathway is abrogated by VHL mutations that disrupt interactions with VDU1. Thus, targeted degradation of VDU1 by pVHL is important in suppressing tumor formation and/or maintenance, and VDU1 may have oncogenic activity that is uncovered in the absence of the functional ligase. VDU1, therefore, is important in neoplastic disease characterized by mutated pVHL (100% of patients with VHL (autosomal dominant) disease), and 50-80% of the far larger number of patients with sporadic renal clear cell carcinoma (Stolle et al., 1998, Hum. Mutat., 12(6):417-423; Gnarra et al., 1994, Nat. Genet., 7(1):85-90.). Inhibition of VDU1 functionally mimics the activity of the wild type tumor suppressor pVHL.

USP7 (also known as HAUSP) and USP2a and Cancer

Deubiquitinating enzymes may serve to spare certain proteins, or at least prolong their cellular lifetime by removing the initial ubiquitin tag, thereby preventing proteasomal degradation. USP7 is known to stabilize the tumor suppressor p53 (Li et al., 2002, supra). USP2a has been implicated in the regulation of fatty acid synthase (FAS), a molecular signature of prostate cancer (Rossi et al., 2003, Mol. Cancer. Res., 1(10):707-715; Agostini et al., 2004, Oral. Oncol., 40(7):728-735; Graner et al., 2004, Cancer Cell, 5(3):253-61.). USP2a is androgen-regulated and over-expressed in prostate cancer, and is thus an oncogenic protein. Thus, depending on the roles of their substrates, deubiquitinating enzymes can be either activated or inhibited to achieve therapeutic effect.

Isopeptidase T and Cardiovascular Disease

The deubiquitinating enzyme Isopeptidase T is down-regulated in patients with chromosome 22q11 deletion syndrome, which encompasses a variety of heart defects (Yamagishi et al., 1999, Science, 283(5405):1158-1161). Along with UFD1, isopeptidase T is down-regulated in myocytes from patients with heart failure (see, e.g., Kostin et al., 2003, Circ. Res., 92(7):715-724). This isopeptidase is known to remove polyubiquitin chains from ubiquitin-protein conjugates and stimulate protein degradation, and its absence results in accumulation of polyubiquitinated proteins and a disruption of the ubiquitin-proteasome degradation pathway, thereby leading to autophagic cell death (Hadari et al., 1992, J. Biol. Chem., 267(2):719-727; Johnson et al., 1995, Biol. Chem., 270(29):17442-17456; Stefanis et al., 2001, J. Neurosci., 21(24):9549-9560).

JAMM Motif Isopeptidase AMSH and Pulmonary Disease and Cancer

A JAMM domain-containing protein is linked with the signal transduction associated with endosomal sorting, i.e., trafficking between the membrane and endosomalaysosomal compartments, of the EGF receptor (EGFR). This protein, AMSH (Associated Molecule with the SH3-domain of STAM), is a protein that regulates receptor sorting at the endosome (McCullough et al., 2004, J. Cell Biol., 166(4):

487-492; Clague et al., 2001, J. Cell Sci., 114(Pt 17):3075-3081). The EGFR regulates numerous cellular functions by initiating signal transduction cascades (Lockhart et al., 2005, Semin. Oncol., 32(1):52-60; von Ahsen et al., 2005, Chembiochem, 6(3):481-490; Leroy et al., 1998, Nature, 395(6701):451-452; Spano et al., 2005, Ann. Oncol., 16(2): 189-194.). During the cellular lifetime of the EGFR, it recycles from membrane to early (sorting) endosome, before finally being selected for sorting to the late endosome and lysosome, where it is degraded by acid proteases. The EGFR participates in signal transduction both at the membrane and in the early endosome compartment. While much of the signaling is concerned with regulation of cell growth and other functions, one component of signal transduction regulates trafficking of the EGFR itself. The E3 ligase Cb1 mediates ubiquitination of phosphorylated EGFR. Subsequent signaling events result in degradation of the receptor in late endosomes/lysosomes. Ub-EGFR is recognized by the protein Hrs at the endosomal surface, and further interactions with the endosomal-associated complex required for transport (ES-CRT) mediated by ubiquitin result in translocation to internal vesicles of the multi-vesicular body (MVB), committing EFGR to protease degradation in the lysosome. Degradation, the end result of Cb1 mediated ubiquitination of EGFR, may be abrogated by a ubiquitin isopeptidase, AMSH, e.g., ablation of AMSH activity by incubation of cells with siRNA leads to increased EGFR degradation; purified AMSH de-ubiquitinates EGFR-Ub in vitro (McCullough et al., 2004, supra). GFR kinase inhibitors and receptor binding antagonists are currently in clinical trial for various cancers (Ciardiello et al., 2001, Clin. Cancer Res., 7(10):2958-2970; LoRusso et al., 2003, Clin. Cancer Res., 9(6):2040-2048). Other disease areas with critical unmet needs are also associated with EGFR activity, such as airway inflammation and mucous hypersecretion associated with bronchial asthma. While asthma is a multifactorial disease, damage of the bronchial epithelium associated with leukocyte infiltration and increased airway responsiveness are consistent features (Puddicombe et al., 2000, FASEB J., 14(10):1362-1374.). The EFGR system has been postulated to play important roles in the growth and differentiation of epithelial and connective tissue cell types in the lung. The EGFR and its ligands are elevated during the pathogenesis of asthma, and induction of this system correlates with goblet cell hyperplasia in asthmatic airways (Takeyama et al., 2001, Am. J. Respir. Crit. Care Med., 163(2):511-516.). Any attempted repair of initial epithelial cell damage leads to hyperproliferation and differentiation responses that are linked to EGFR and EGFR activation (Bonner, 2002, Am. J. Physiol. Lung Cell Mol. Physiol., 283(3):L528-530). Asthmatics appear to develop chronically high levels of EGFR even in undamaged epithelium. This sustains a constant inflammatory condition, and leads to fibrosis and mucus hypersecretion associated with airway obstruction, morbidity and lethality in asthma, COPD, and other pulmonary diseases.

UCHL1 and Parkinson's Disease

UCHL1, or ubiquitin carboxy terminal hydrolase, is genetically associated with Parkinson's Disease (PD) (Chung et al., 2003, J. Neurol., 250 Suppl. 3:11115-11124; Toda et al., 2003, J. Neurol., 250 Suppl. 3:11140-11143; Maraganore et al., 2004, Ann. Neurol., 55(4):512-521). Mutations in UCHL1 cause autosomal dominant PD, consistent with the notion that derangements in the ubiquitin proteasomal pathway play important roles in the demise of dopamine neurons in PD.

Other proteolytic enzymes are associated with other diseases, as is known in the art. Examples of isopeptidases associated with diseases or physiological conditions are as follows.

USP2a prostatic cancer
Ap-UCH essential for long-term memory in Aplysia
BAP 1 tumor suppressor (associates with BRCA1)
CYLD1 tumor suppressor
DUB-1 cytokine-inducible, B-cell selective
DUB-2 cytokine-inducible, T-cell selective
D-ubp-64E Drosophila inhibitor of position-effect variegation
FAF (Fat facets) Drosophila eye development
FAM pre-implantation mouse embryo development
HAUSP (USP7) tumor suppressor (p53 stabilization)
USP10 p53 regulator; DNA damage
Tre-2 (USP6) oncoprotein
Ubp3 inhibitor of transcriptional silencing in yeast
UBP41 apoptosis, bone formation
UBP43 negative regulator of IFN signaling, hematopoesis
UBP45 myogenesis
UBP69 myogenesis
UbpB (Dictyostelium) developmental timing and spatial patterning
UBP-M (USP16) cell cycle control (chromatin condensation)
UBPY cell cycle/cell growth
USP14 (ataxia) synaptic function
UCH-L1 (PGP9.5) Parkinson's Disease, gracile axonal dystrophy
VDU1 (USP20) tumorigenesis (associates with von Hippel-Lindau protein)
VDU2 (USP33) tumorigenesis (associates with von Hippel-Lindau protein)

Kits

The present invention also provides kits for detecting isopeptidase activity. In some embodiments, the kits comprise one or more isopeptidase substrates as described hereinabove. In some embodiments, the kits will comprise a microarray of the diubiquitin substrates. The kits may optionally comprise one or more isopeptidase or deubiquitinase enzymes, and may optionally comprise instructions. Isopeptidase or deubiquitinase enzymes optionally included in the kit include, but are not limited to USP2core, USP7, USP8, USP34, Otub2, JosD1, JosD2, AMSH, Ataxin3, Ataxin3-like, USP20, USP14, A20 and SENP5.

Optional instructions may explain how to conduct the assay, how to detect fluorescence, and/or how to correlate fluorescence to isopeptidase activity. Other optional reagents in the kit can include appropriate buffers for isopeptidase activity.

As used herein, "instructions" or "instructional material" includes a publication, a recording, a diagram, or any other medium of expression which can be used to communicate the usefulness of the composition of the invention for performing a method of the invention. The instructions or instructional material of a kit of the invention can, for example, be affixed to a container which contains a kit of the invention to be shipped together with a container which contains the kit. Alternatively, the instructions or instructional material can be shipped separately from the container with the intention that the instructions or instructional material and kit be used cooperatively by the recipient.

Definitions

As used herein, the phrases "fluorescence resonance energy transfer", "Förster resonance energy transfer", and "FRET" refer to the energy transfer from an excited fluorescent group to, at least partially, a quenching group. The quenching group may radiate the absorbed light as light of a different wavelength or dissipate it as heat. FRET depends on 1) an overlap between the emission spectrum of the fluorescent group and the absorption spectrum of the quenching group and 2) the distance between the quenching group and the fluorescent group. Above a certain critical distance, the quenching group is unable to absorb the light emitted by the fluorescent group.

As used herein, the term "fluorescent group" (sometimes referred to as a fluorophore or FRET donor) refers to a molecule that, when excited with light having a selected wavelength, emits light of a different wavelength.

As used herein, the term "quenching group" (sometimes referred to as a FRET acceptor) refers to any fluorescence-modifying group that can attenuate at least partly the energy/light emitted by a fluorescent group. Illumination of the fluorescent group in the presence of the quenching group leads to an emission signal that is less intense than expected or completely absent. Depending on the identity of the quenching group, the fluorescence emission can undergo a number of alterations, including, but not limited to, attenuation, complete quenching, a shift in wavelength, a shift in polarity, and a change in fluorescence lifetime.

As used herein, the term "energy transfer pair" refers to any two molecules that participate in fluorescence resonance energy transfer. The energy transfer pair is typically two molecules that participate in fluorescence resonance energy transfer, but the instant invention also encompasses the use of multiple fluorescent groups and/or quenching groups within an energy transfer complex. The energy transfer pair may comprise a first energy transfer pair member and a second energy transfer pair member. Preferably, an energy transfer pair comprises a fluorescent group and a quenching group. While the first energy transfer pair member is typically different than the second energy transfer pair member, they may be the same.

As used herein, the term "microarray" refers to an ordered arrangement of array elements. The array elements are arranged so that there are at least one or more different array elements. The array elements may be contained within/on a solid support and need not be immobilized on the solid support. For example, an array of substrates in solution may be contained in a microtiter plate. The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish/plate.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, a "biological sample" refers to a sample of biological material obtained from a subject, particularly a human subject, including a tissue, a tissue sample, a cell sample, a tumor sample, and a biological fluid (e.g., blood or urine). A biological sample may be obtained in the form of, e.g., a tissue biopsy, such as, an aspiration biopsy, a brush biopsy, a surface biopsy, a needle biopsy, a punch biopsy, an excision biopsy, an open biopsy, an incision biopsy and an endoscopic biopsy.

As used herein, the terms "modified," "engineered," or "mutant" refer to altered polynucleotide or amino acid sequences. In one embodiment, a polynucleotide sequence encoding a ubiquitin is modified/engineered/mutated by introducing one or more mutations, particularly by site directed mutagenesis. Additionally, libraries of mutant polynucleotides comprising at least one mutation may also be prepared using random mutagenesis or DNA shuffling techniques. In a particular embodiment, the random mutagenesis is limited to desired regions of the polynucleotide, particularly the region(s) believed to encode the amino acids responsible for the interaction between ubiquitin and DUB. Common mutagenesis techniques are described in Current Protocols in Molecular Biology, Ausubel, F. et al. eds., John Wiley (2006) and U.S. Pat. Nos. 5,605,793; 5,811,238; 5,830,721; 5,834,252; and 5,837,458. As used herein, a "mutation" or "alteration" refers to a variation in the nucleotide or amino acid sequence of a gene as compared to the naturally occurring or normal nucleotide or amino acid sequence. A mutation may result from the deletion, insertion or substitution of at least one nucleotide or amino acid. In a particular embodiment, the mutation is a substitution (i.e., the replacement of at least one nucleotide or amino acid with a different nucleotide(s) or amino acid residue(s)).

The term "operably linked" refers to a juxtaposition/linkage wherein the components so described are in a relationship permitting them to function in their intended manner.

The following examples are provided to illustrate various embodiments of the present invention. The examples are illustrative and are not intended to limit the invention in any way.

EXAMPLE 1

Derivatization of Ubiquitin K48R, K63R, K11C with QXL™ 570 C2 Maleimide (Ub1C11$_{Q570}$)

Purified ubiquitin K48R, K63R, K11C at a concentration between 5 and 20 mg/mL in phosphate buffered saline (PBS) was mixed with QXL™ 570 C2 maleimide (AnaSpec, Inc., Fremont, Calif.; 40 mM in DMSO) at a molar ratio of 4:1 (QXL™:ubiquitin). The sample was incubated at room temperature for 1 hour and the extent of modification was determined by LC-MS analysis. Typically, the reaction proceeded to ≥95% completion. Modified ubiquitin K48R, K63R, C11Q$_{570}$ was separated from free QXL™ 570 by chromatography on a PD-10 desalting column (GE Healthcare; Waukesha, Wis.) using PBS as the running buffer. The calculated mass of ubiquitin K48R, K63R, C11$_{Q570}$ is 9386.9 Da. The observed mass was 9387.2±0.1 Da. Pooled fractions from the PD-10 column were concentrated to >20 mg/mL using a centrifugal concentrator (Millipore; Billerica, Mass.) and stored at +4° C. for use in a conjugation reaction.

EXAMPLE 2

Derivatization of Ubiquitin K48C, K63R with QXL™ 570 C2 Maleimide (Ub1C48$_{Q570}$)

Purified ubiquitin K48C, K63R at a concentration between 5 and 20 mg/mL in phosphate buffered saline (PBS) was mixed with QXL™ 570 C2 maleimide (AnaSpec, Inc., 40 mM in DMSO) at a molar ratio of 4:1 (QXL™:ubiquitin). The sample was incubated at room temperature for 1 hour and the extent of modification was determined by LC-MS analysis. Typically, the reaction proceeded to >95% completion. Modified ubiquitin C48$_{Q570}$, K63R was separated from free QXL™ 570 by chromatography on a PD-10 desalting column (GE Healthcare) using PBS as the running buffer. The calculated mass of ubiquitin C48$_{Q570}$, K63R is 9358.9 Da. The observed mass was 9358.1±0.1 Da. Pooled fractions from the PD-10 column were concentrated to >20 mg/mL using a centrifugal concentrator (Millipore) and stored at +4° C. for use in a conjugation reaction.

EXAMPLE 3

Derivatization of Ubiquitin K48R, K63C with QXL™ 570 C2 Maleimide (Ub1C63$_{Q570}$)

Purified ubiquitin K48R, K63C at a concentration between 5 and 20 mg/mL in phosphate buffered saline (PBS) was mixed with QXL™ 570 C2 maleimide (AnaSpec, Inc., 40 mM in DMSO) at a molar ratio of 4:1 (QXL™:ubiquitin). The sample was incubated at room temperature for 1 hour and the extent of modification was determined by LC-MS analysis. Typically, the reaction proceeded to >95% completion. Modified ubiquitin K48R, C63$_{Q570}$ was separated from free QXL™ 570 by chromatography on a PD-10 desalting column (GE Healthcare) using PBS as the running buffer. The calculated mass of ubiquitin K48R, C63$_{Q570}$ is 9358.9 Da. The observed mass was 9358.8±0.3 Da. Pooled fractions from the PD-10 column were concentrated to >20 mg/mL using a centrifugal concentrator (Millipore) and stored at +4° C. for use in a conjugation reaction.

EXAMPLE 4

Derivatization of Ubiquitin K11C, G75A, G76A with TAMRA C2 Maleimide (Ub2C11$_{TAMRA}$)

Purified ubiquitin K11C, G75A, G76A, at a concentration between 5 and 20 mg/mL in phosphate buffered saline (PBS) was mixed with tetramethylrhodamine (TAMRA) C2 maleimide (AnaSpec, Inc., 40 mM in DMSO) at a molar ratio of 4:1 (TAMRA:ubiquitin). The sample was incubated at room temperature for 1 hour and the extent of modification was determined by LC-MS analysis. Typically, the reaction proceeded to >95% completion. Modified ubiquitin C11$_{TAMRA}$, G75A, G76A was separated from free TAMRA by chromatography on a PD-10 desalting column (GE Healthcare) using PBS as the running buffer. The calculated mass of ubiquitin C11$_{TAMRA}$, G75A, G76A is 9120.5 Da. The observed mass was 9120.9±0.1 Da. Pooled fractions from the PD-10 column were concentrated to >20 mg/mL using a centrifugal concentrator (Millipore) and stored at +4° C. for use in a conjugation reaction.

EXAMPLE 5

Derivatization of Ubiquitin S20C, G75A, G76A with TAMRA C2 Maleimide (Ub2C20$_{TAMRA}$)

Purified ubiquitin S20C, G75A, G76A at a concentration between 5 and 20 mg/mL in phosphate buffered saline (PBS) was mixed with TAMRA C2 maleimide (AnaSpec, Inc., 40 mM in DMSO) at a molar ratio of 4:1 (TAMRA:ubiquitin). The sample was incubated at room temperature for 1 hour and the extent of modification was determined by LC-MS analysis. Typically, the reaction proceeded to >95% completion. Modified ubiquitin C20$_{TAMRA}$, G75A, G76A was separated from free TAMRA by chromatography on a PD-10 desalting column (GE Healthcare) using PBS as the running buffer. The calculated mass of ubiquitin C20$_{TAMRA}$, G75A, G76A is 9161.6 Da. The observed mass was 9162.0±0.2 Da. Pooled fractions from the PD-10 column were concentrated to >20 mg/mL using a centrifugal concentrator (Millipore) and stored at +4° C. for use in a conjugation reaction.

EXAMPLE 6

Derivatization of Ubiquitin K48R, K63R, S57C with QXL™490 C2 Maleimide (Ub1C57$_{Q490}$)

Purified ubiquitin K48R, K63R, S57C at a concentration between 5 and 20 mg/mL in phosphate buffered saline (PBS) was mixed with QXL™ 490 C2 maleimide (AnaSpec, Inc., 40 mM in DMSO) at a molar ratio of 4:1 (QXL™:ubiquitin). The sample was incubated at room temperature for 1 hour and the extent of modification was determined by LC-MS analysis. Typically, the reaction proceeded to >95% completion. Modified ubiquitin C57$_{Q490}$, K48R, K63R was separated from free QXL™ 490 by chromatography on a PD-10 desalting column (GE Healthcare) using PBS as the running buffer. The calculated mass of ubiquitin C57$_{Q490}$, K48R K63R is 9207.5 Da. The observed mass was 9209.1 Da. Pooled fractions from the PD-10 column were concentrated to >20 mg/mL using a centrifugal concentrator (Millipore) and stored at +4° C. for use in a conjugation reaction.

EXAMPLE 7

Derivatization of Ubiquitin K48R, K63R, S57C with QXL™570 C2 Maleimide (Ub1C57$_{Q570}$)

Purified ubiquitin K48R, K63R, S57C at a concentration between 5 and 20 mg/mL in phosphate buffered saline (PBS) was mixed with QXL™ 570 C2 maleimide (AnaSpec, Inc., 40 mM in DMSO) at a molar ratio of 4:1 (QXL™:ubiquitin). The sample was incubated at room temperature for 1 hour and the extent of modification was determined by LC-MS analysis. Typically, the reaction proceeded to >95% completion. Modified ubiquitin C57$_{Q570}$, K48R, K63R was separated from free QXL™570 by chromatography on a PD-10 desalting column (GE Healthcare) using PBS as the running buffer. The calculated mass of ubiquitin C57$_{Q570}$, K48R K63R is 9428.0 Da. The observed mass was 9429.1 Da. Pooled fractions from the PD-10 column were concentrated to >20 mg/mL using a centrifugal concentrator (Millipore) and stored at +4° C. for use in a conjugation reaction.

EXAMPLE 8

Derivatization of Ubiquitin K48R, K63R, S57C with Dabcyl C2 Maleimide (Ub1C57$_{Dabcyl}$)

Purified ubiquitin K48R, K63R, S57C at a concentration between 5 and 20 mg/mL in phosphate buffered saline (PBS) was mixed with Dabcyl C2 maleimide (AnaSpec, Inc., 40 mM in DMSO) at a molar ratio of 4:1 (Dabcyl:ubiquitin). The sample was incubated at room temperature for 1 hour and the extent of modification was determined by LC-MS analysis. Typically, the reaction proceeded to ≥95% completion. Modified ubiquitin C57$_{Dabcyl}$, K48R, K63R was separated from free Dabcyl by chromatography on a PD-10 desalting column (GE Healthcare) using PBS as the running buffer. The calculated mass of ubiquitin C57$_{Dabcyl}$, K48R K63R is 9028.4 Da. The observed mass was 9028.8 Da. Pooled fractions from the PD-10 column were concentrated to >20 mg/mL using a centrifugal concentrator (Millipore) and stored at +4° C. for use in a conjugation reaction.

EXAMPLE 9

Derivatization of Ubiquitin K48R, K63R, S57C with Fluorescein Maleimide (Ub1C57$_{Fluor}$)

Purified ubiquitin K48R, K63R, S57C at a concentration between 5 and 20 mg/mL in phosphate buffered saline (PBS) was mixed with fluoroscein maleimide (AnaSpec, Inc., 40 mM in DMSO) at a molar ratio of 4:1 (fluoroscein:ubiquitin). The sample was incubated at room temperature for 1 hour and the extent of modification was determined by LC-MS analysis. Typically, the reaction proceeded to ≥95% completion. Modified ubiquitin C57$_{Fluor}$, K48R, K63R was separated from free fluoroscein by chromatography on a PD-10 desalting column (GE Healthcare) using PBS as the running buffer. The calculated mass of ubiquitin C57$_{Fluor}$, K48R K63R is 9064.3 Da. The observed mass was 9064.3 Da. Pooled fractions from the PD-10 column were concentrated to >20 mg/mL using a centrifugal concentrator (Millipore) and stored at +4° C. for use in a conjugation reaction.

EXAMPLE 10

Derivatization of Ubiquitin S20C, G75A, G76A with EDANS C2 Maleimide (Ub2C20$_{EDANS}$)

Purified ubiquitin S20C, G75A, G76A at a concentration between 5 and 20 mg/mL in phosphate buffered saline (PBS) was mixed with EDANS C2 maleimide (AnaSpec, Inc., 40 mM in DMSO) at a molar ratio of 4:1 (EDANS:ubiquitin). The sample was incubated at room temperature for 1 hour and the extent of modification was determined by LC-MS analysis. Typically, the reaction proceeded to ≥95% completion. Modified ubiquitin C20$_{EDANS}$, G75A, G76A was separated from free EDANS by chromatography on a PD-10 desalting column (GE Healthcare) using PBS as the running buffer. The calculated mass of ubiquitin C20$_{EDANS}$, G75A, G76A is 8914.2 Da. The observed mass was 8914.7 Da. Pooled fractions from the PD-10 column were concentrated to >20 mg/mL using a centrifugal concentrator (Millipore) and stored at +4° C. for use in a conjugation reaction.

EXAMPLE 11

Synthesis of K48-linked Diubiquitins from Ub1C11$_{Q570}$ and Ub2C11$_{TAMRA}$

Ub1C11$_{Q570}$ and Ub2C11$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 (ubiquitin activating enzyme (E1)) and 20 µM E2-25K (E2 enzyme which can catalyze in vitro the unanchored polyUb; Hip2). The conjugation reaction was done at 37° C. from 4-15 hours. Progress of the reaction was monitored by LC-MS analysis. When the reaction proceeded to ≥90% completion (at least 90% of the Ub1C11$_{Q570}$ has been used), the diubiquitin is separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q11T11 (DiUb48-1) is 18,489.3 Da. The observed mass was 18,490.3±0.3 Da.

EXAMPLE 12

Synthesis of K48-linked Diubiquitins from Ub1C48$_{Q570}$ and Ub2C11$_{TAMRA}$

Ub1C48$_{Q570}$ and Ub2C11$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM E2-25K. The conjugation reaction was done at 37° C. from 4-15 hours. Progress of the reaction was monitored by LC-MS analysis. When the reaction has proceeded to ≥90% completion (at least 90% of the Ub1C48$_{Q570}$ was used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q48T11 (DiUb48-3) is 18,461.3 Da. The observed mass was 18,461.5±0.1 Da.

EXAMPLE 13

Synthesis of K48-linked Diubiquitins from Ub1C63$_{Q570}$ and Ub2C11$_{TAMRA}$

Ub1C63$_{Q570}$ and Ub2C11$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM E2-25K. The conjugation reaction is done at 37° C. from 4-15 hours. Progress of the reaction is monitored by LC-MS analysis. When the reaction has proceeded to ≥90% completion (at least 90% of the Ub1C63$_{Q570}$ has been used), the diubiquitin is separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q63T11 (DiUb48-6) is 18,461.3 Da. The observed mass was 18,462.2±0.2 Da.

EXAMPLE 14

Synthesis of K48-linked Diubiquitins from Ub1C11$_{Q570}$ and Ub2C20$_{TAMRA}$

Ub1C11$_{Q570}$ and Ub2C20$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM E2-25K. The conjugation reaction was done at 37° C. from 4-15 hours. Progress of the reaction has been monitored by LC-MS analysis. When the reaction has proceeded to ≥90% completion (at least 90% of the Ub1C11$_{Q570}$ has been used), the diubiquitin is separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q11T20 (DiUb48-2) is 18,530.4 Da. The observed mass was 18,531.0±0.1 Da.

EXAMPLE 15

Synthesis of K48-linked Diubiquitins from Ub1C48$_{Q570}$ and Ub2C20$_{TAMRA}$

Ub1C48$_{Q570}$ and Ub2C20$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation is initiated by the addition of 0.1 µM Ube1 and 20 µM E2-25K. The conjugation reaction was done at 37° C. from 4-15 hours. Progress of the reaction is monitored by LC-MS analysis. When the reaction proceeded to ≥90% completion (at least 90% of the Ub1C48$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q48T20 (DiUb48-4) is 18,502.4 Da. The observed mass was 18,502.8±0.2 Da.

EXAMPLE 16

Synthesis of K48-linked Diubiquitins from Ub1C63$_{Q570}$ and Ub2C20$_{TAMRA}$

Ub1C63$_{Q570}$ and Ub2C20$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM E2-25K. The conjugation reaction was done at 37° C. from 4-15 hours. Progress of the reaction was monitored by LC-MS analysis. When the reaction proceeded to ≥90% completion (at least 90% of the Ub1C63$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q63T20 (DiUb48-6) is 18,502.4 Da. The observed mass was 18,503.4±0.1 Da.

EXAMPLE 17

Synthesis of K63 Linked Diubiquitins from Ub1C11$_{Q570}$ and Ub2C11$_{TAMRA}$

Ub1C11$_{Q570}$ and Ub2C11$_{TAMRA}$ were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to ≥90% completion (at least 90% of the Ub1C11$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q11T11 (DiUb63-1) is 18,489.3 Da. The observed mass was 18,489.5±0.1 Da.

EXAMPLE 18

Synthesis of K63 Linked Diubiquitins from Ub1C48$_{Q570}$ and Ub2C11$_{TAMRA}$

Ub1C48$_{Q570}$ and Ub2C11$_{TAMRA}$ 1 were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to ≥90% completion (at least 90% of the Ub1C48$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q48T11 (DiUb63-3) is 18,461.3 Da. The observed mass was 18,461.7±0.1 Da.

EXAMPLE 19

Synthesis of K63 Linked Diubiquitins from Ub1C63$_{Q570}$ and Ub2C11$_{TAMRA}$

Ub1C63$_{Q570}$ and Ub2C11$_{TAMRA}$ were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to >90% completion (at least 90% of the Ub1C63$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q63T11 (DiUb63-5) is 18,461.3 Da. The observed mass was 18,462.3±0.04 Da.

EXAMPLE 20

Synthesis of K63 Linked Diubiquitins from Ub1C11$_{Q570}$ and Ub2C20$_{TAMRA}$

Ub1C11$_{Q570}$ and Ub2C20$_{TAMRA}$ were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to ≥90% completion (at least 90% of the Ub1C11$_{Q520}$1 has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q11T20 (DiUb63-2) is 18,530.4 Da. The observed mass was 18,530.6±0.2 Da.

EXAMPLE 21

Synthesis of K63 Linked Diubiquitins from Ub1C48$_{Q570}$ and Ub2C20$_{TAMRA}$

Ub1C48$_{Q570}$ and Ub2C20$_{TAMRA}$ were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to ≥90% completion (at least 90% of the Ub1C48$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q48T20 (DiUb63-4) is 18,502.4 Da. The observed mass was 18,502.5±0.2 Da.

EXAMPLE 22

Synthesis of K63 Linked Diubiquitins from Ub1C63$_{Q570}$ and Ub2C20$_{TAMRA}$

Ub1C63$_{Q570}$ and Ub2C20$_{TAMRA}$ were combined in a molar ratio of 1:1.1 at a final concentration between 0.5 and 0.9 mM in a reaction buffer containing 50 mM Tris pH 7.5, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation was initiated by the addition of 0.1 µM Ube1 and 20 µM of the heterodimeric Ubc13/Mms2 complex. The conjugation reaction was done at 37° C. from 4-15 hours. Progress of the reaction is monitored by LC-MS analysis. When the reaction proceeded to ≥90% completion (at least 90% of the Ub1C63$_{Q570}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K63-linked diubiquitin Q63T20 (DiUb63-6) is 18,502.4 Da. The observed mass was 18,503.4±0.04 Da.

EXAMPLE 23

Synthesis of K48-linked Diubiquitins from Ub1C57$_{Q570}$ and Ub2C20$_{TAMRA}$

Ub1Q57 and Ub2T20 were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation is initiated by the addition of 0.1 µM Ube1 and 20 µM E2-25K. The conjugation reaction was done at 37° C. for 4-15 hours. Progress of the reaction is monitored by LC-MS analysis. When the reaction proceeded to ≥90% completion (at least 90% of the Ub1Q57 has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin Q57T20 (DiUb48-8) is 18,589.5 Da. The observed mass was 18,590.5 Da.

EXAMPLE 24

Synthesis of K48-linked Diubiquitins from Ub1C57$_{Fluor}$ and Ub2C20$_{TAMRA}$

Ub1C57$_{Fluor}$ and Ub2C20$_{TAMRA}$ were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.5 U/ml inorganic pyrophosphatase, and 0.5 U/ml creatine phosphokinase. Conjugation is initiated by the addition of 0.1 µM Ube1 and 20 µM E2-25K. The conjugation reaction was done at 37° C. from 4-15 hours. Progress of the reaction is monitored by LC-MS analysis. When the reaction proceeded to ≥90% completion (at least 90% of the Ub1C57$_{Fluor}$ has been used), the diubiquitin was separated from monomeric ubiquitins by chromatography on a strong cation exchange column in 50 mM Mes, pH 5.5-6. Monomeric ubiquitin is not retained under these conditions while salt (increased ionic strength) is required to elute the diubiquitin. The calculated mass of K48-linked diubiquitin F57T20 (DiUb48-9) is 18,225.9 Da. The observed mass was 18,226.2 Da.

EXAMPLE 25

Cleavage of Diubiquitins by USP2core

Figure 3A:
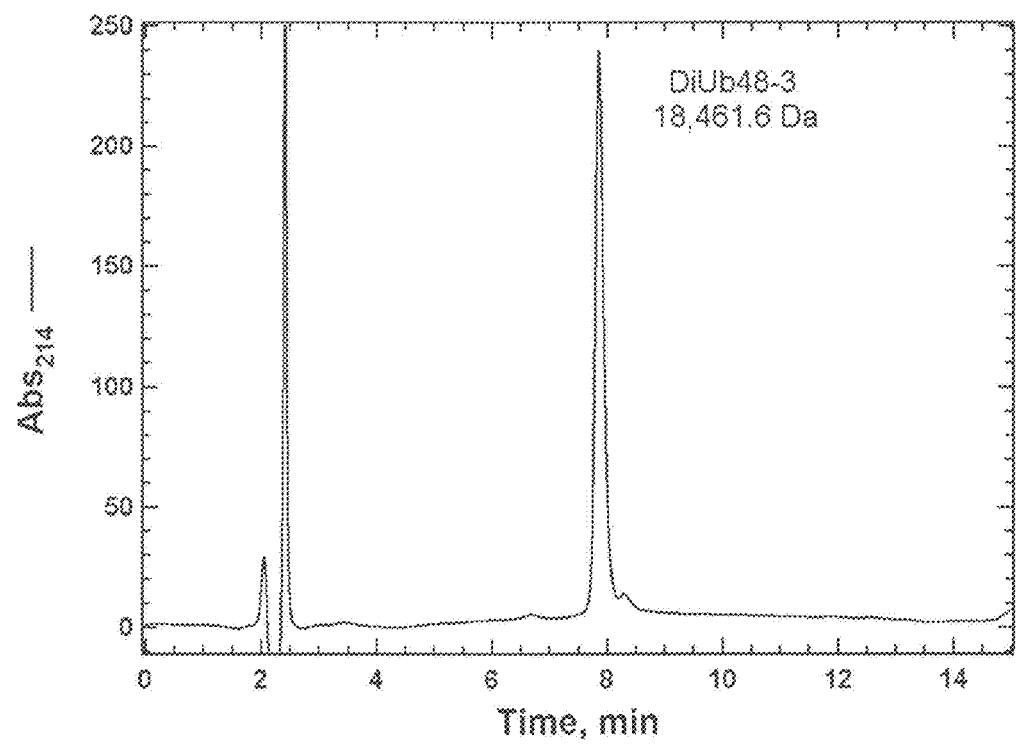
FIG. 3 shows the liquid chromatography-mass spectrometry (LC-MS) analysis of K48 linked IQF-diubiquitin Q48T11 before (FIG. 3A) and after (FIG. 3B) treatment with USP2core.
Figure 3B:
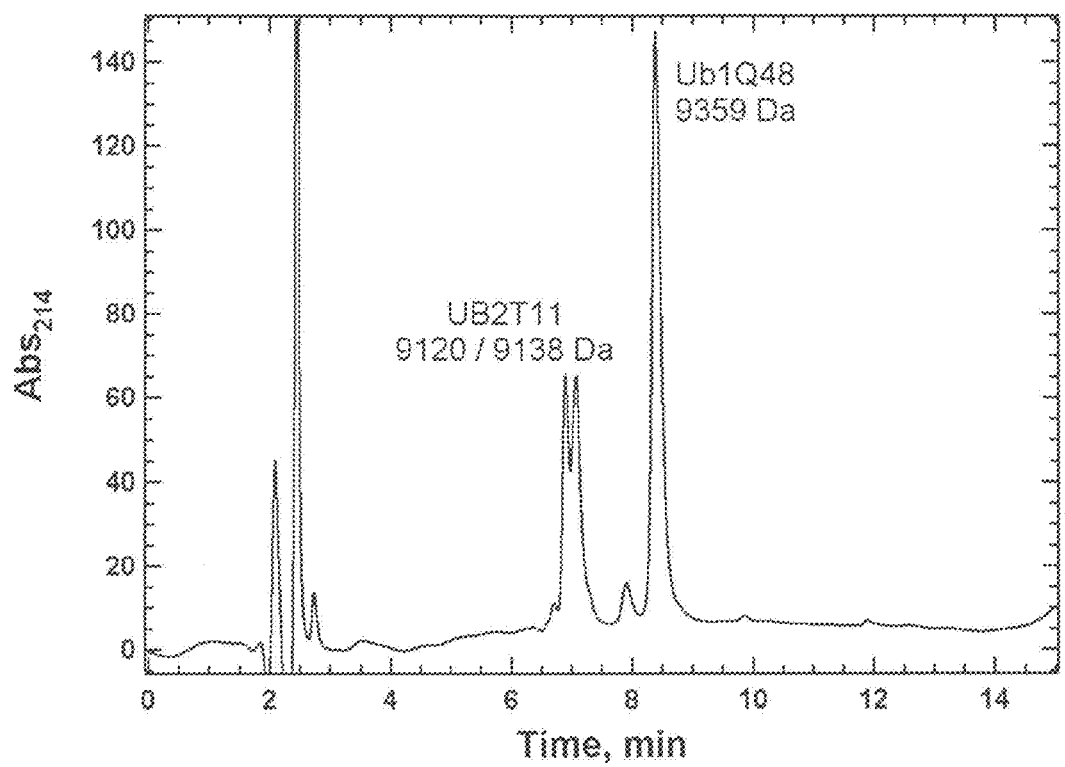

FIG. 3 shows the liquid chromatography-mass spectrometry (LC-MS) analysis of K48 linked IQF-diubiquitin Q48T11 before (FIG. 3A) and after (FIG. 3B) treatment with USP2core.

Figure 4A:
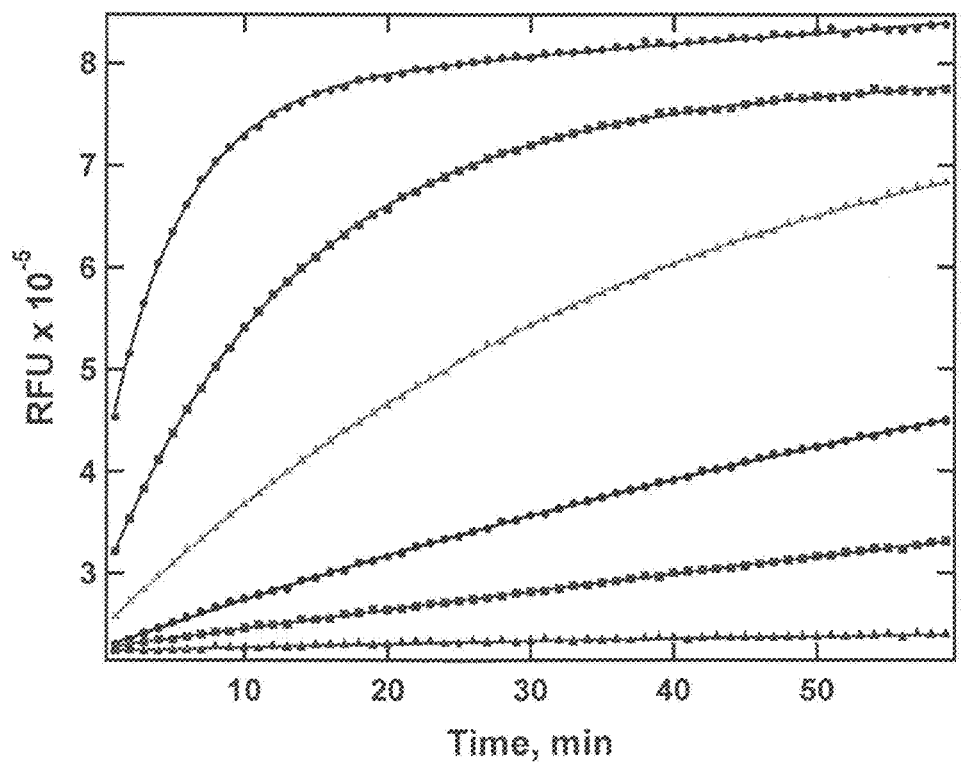
FIG. 4A provides a time course of different concentrations of USP2core (96, 29.8, 9.2, 2.9, 0.89, 0.28 nM; top to bottom).
Figure 4B:
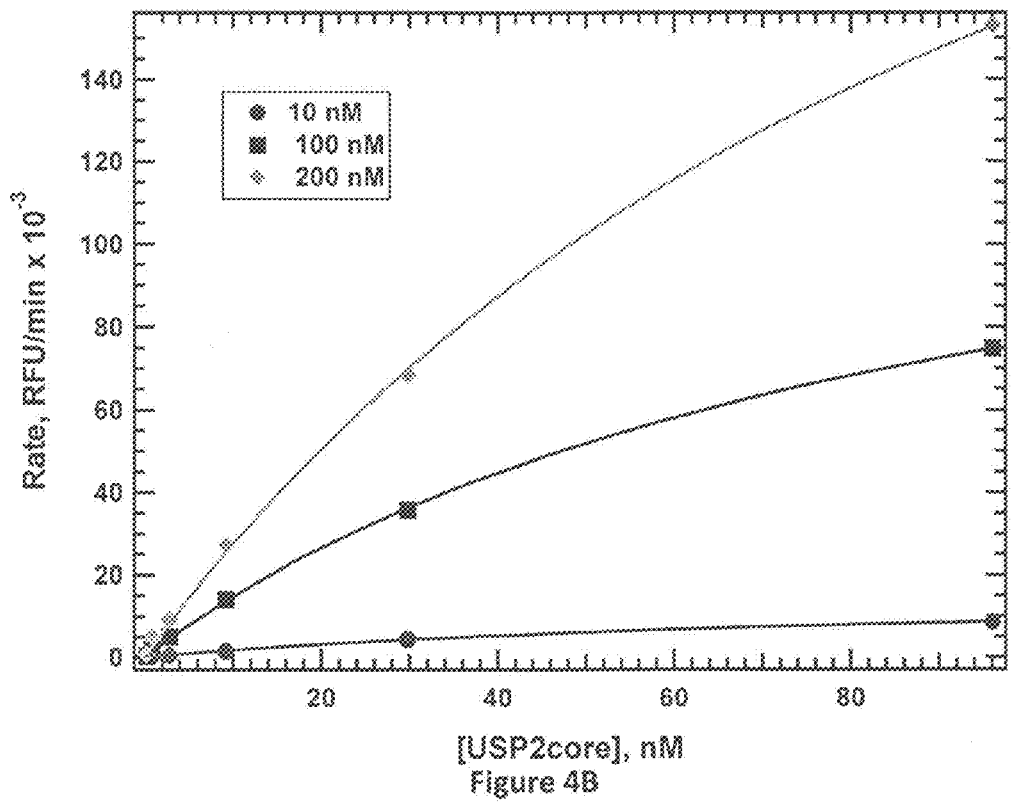
FIG. 4B shows different concentrations of USP2core with different concentrations of the same substrate (200, 100, 10 nM).

FIG. 4 presents graphs demonstrating the increase in fluorescence upon cleavage of K48 linked IQF-diubiquitin Q63T11 (DiUb48-5) by USP2core. FIG. 4A provides a time course of different concentrations of USP2core (96, 29.8, 9.2, 2.9, 0.89, 0.28 nM; top to bottom). FIG. 4B shows different concentrations of USP2core with different concentrations of the same substrate (200, 100, 10 nM).

Figure 5A:
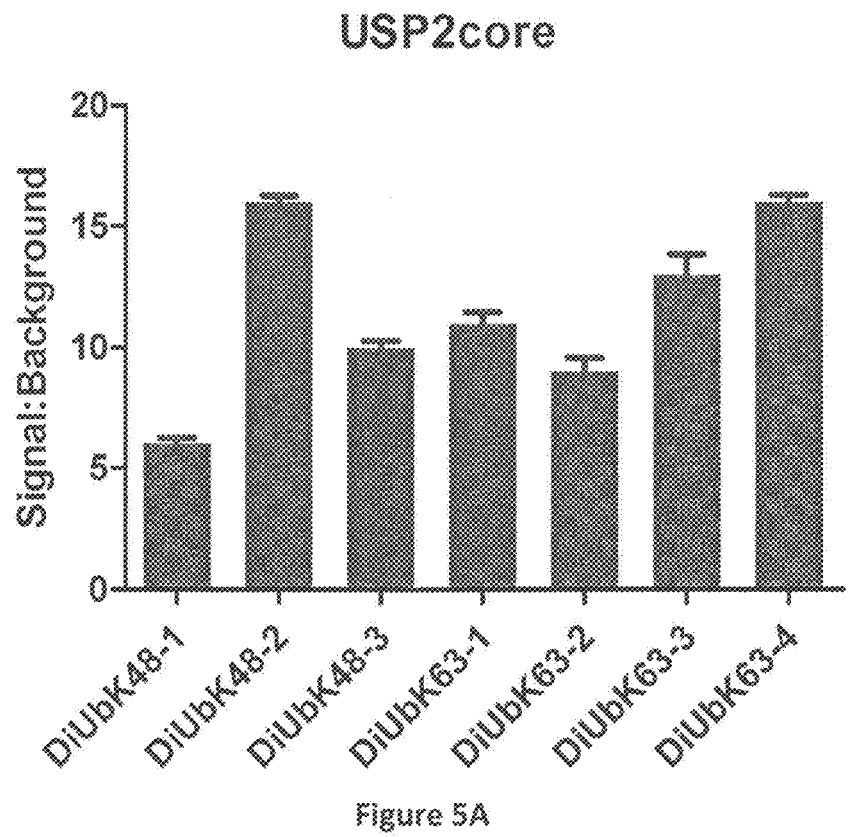
FIG. 5 shows the differential cleavage of different K48 linked- and K63 linked-diubiquitins by USP2core (upper panel) or AMSHcore (lower panel). K48 linked-IQF diubiquitins are abbreviated as DiUb48 and K63 linked IQF-diubiquitins as DiUb63. In both cases $-1=Q11T11$, $-2=Q11T20$, $-3=Q48T11$, and $-4=Q48T20$ derivatives ($Q=QXL^{TM}$ 570, $T=TAMRA$, and the number indicates the site of attachment).
Figure 5B:
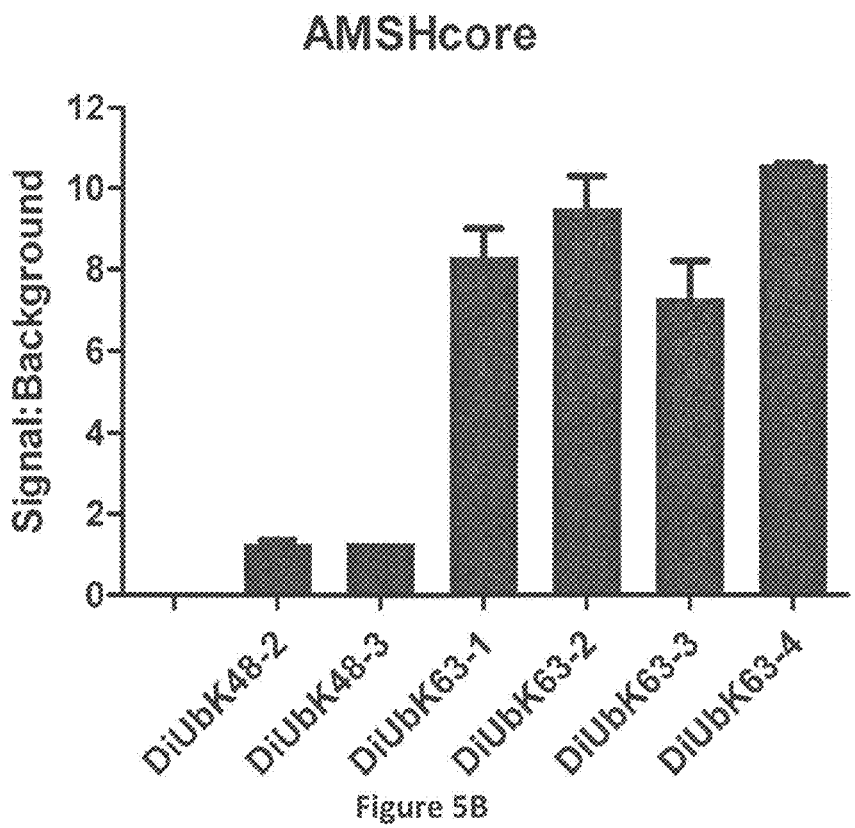

FIG. 5 shows the differential cleavage of different K48 linked- and K63 linked-diubiquitins by USP2core (upper panel) or AMSHcore (lower panel). K48 linked-IQF diubiquitins are abbreviated as DiUb48 and K63 linked IQF-diubiquitins as DiUb63. In both cases −1=Q11T11, −2=Q11T20, −3=Q48T11, and −4=Q48T20 derivatives (Q=QXL™ 570, T=TAMRA, and the number indicates the site of attachment). Table 2 shows the cleavage of diubiquitins by different DUBs and shows the selectivity of different DUBs for the diubiquitin substrates. AMSHcore, a known K63 linkage specific DUB, only cleaves members of the K63 linked IQF-diubiquitins, while OTUB1, a K48 linkage specific DUB, only cleaves members of the K48 linked IQF-diubiquitins. USP2core and USP7, which show no linkage preferences, cleave both classes of IQF-diubiquitins.

TABLE 2

Cleavage of diubiquitins by different DUBs.

|  | AMSHcore | USP2core | Otub1 | USP7 |
|---|---|---|---|---|
| DiUb48-1 | − | +++ | − | + |
| DiUb48-2 | − | +++ | + | + |
| DiUb48-3 | − | +++ | + | + |
| DiUb63-1 | ++ | +++ | − | + |
| DiUb63-2 | ++ | +++ | − | + |
| DiUb63-3 | + | +++ | − | + |

− = no cleavage, + = low cleavage, ++ = moderate cleavage, +++ = strong cleavage.

Figure 6A:
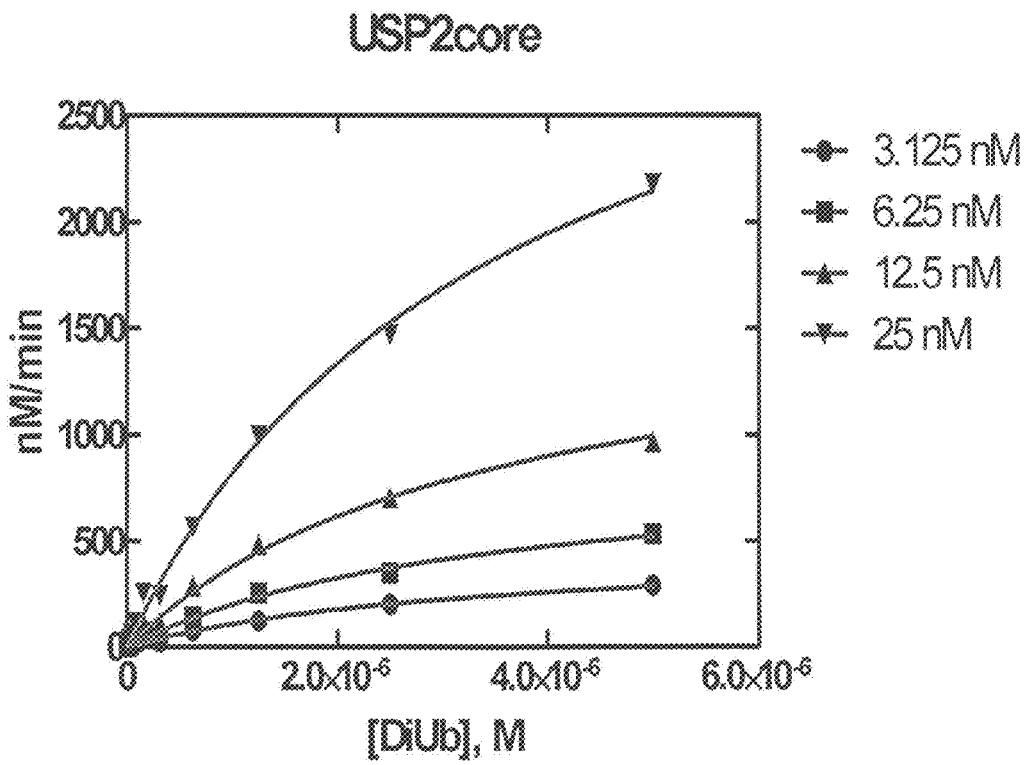
FIGS. 6A and 6B show the determination of the standard Michaelis-Menten kinetic parameters ($k_m$ and $k_{cat}$) for K48 linked IQF-diubiquitin $C48_{Q570}C20_{TAMRA}$ (DiUb48-4) with USP2core.
Figure 6B:
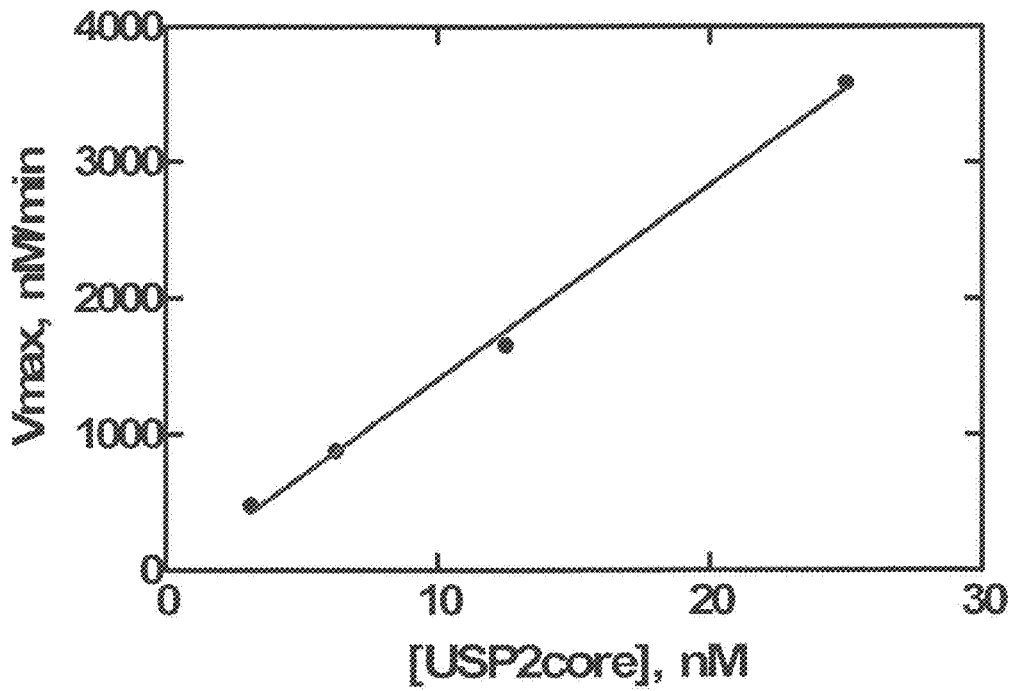

The diubiquitin substrate was used to construct a 12-step, two-fold serial dilution series in the wells of a black microtiter plate from 8 µM to 3.9 nM. USP2core was diluted to 50, 25, 12.5, and 6.25 nM in an assay buffer consisting of 50 mM Tris-HCl, pH 8.0, 100 mM NaCl, 5 mM DTT, and 0.05% CHAPS. At zero time, 50 µL was added to 50 µL of the diubiquitin substrate dilutions and the increase in fluorescence with time was monitored by measuring the total fluorescence in each well at 1 minute intervals for 60 minutes. These data were used to determine the rates of cleavage of the substrates at for each substrate and enzyme concentration. Plots of rate versus substrate concentration were constructed for each enzyme concentration and the kinetic parameters Km and Vmax were determined by fitting these plots the Michaelis-Menten equation using a non-linear least squares fitting algorithm. Plots of Vmax versus enzyme concentration were used to determine psuedo kcat (turnover rates) for the enzyme. For instance, the Km calculated for the K48 linked diubiquitin Q48T20 was 3.37±0.2 µM and the kcat was 2.38 s$^{-1}$. FIGS. 6A and 6B show the determination of the standard Michaelis-Menten kinetic parameters ($k_M$ and $k_{cat}$) for K48 linked IQF-diubiquitin C48$_{Q570}$C20$_{TAMRA}$ (DiUb48-4) with USP2core.

EXAMPLE 26

Quenching

Figure 7:
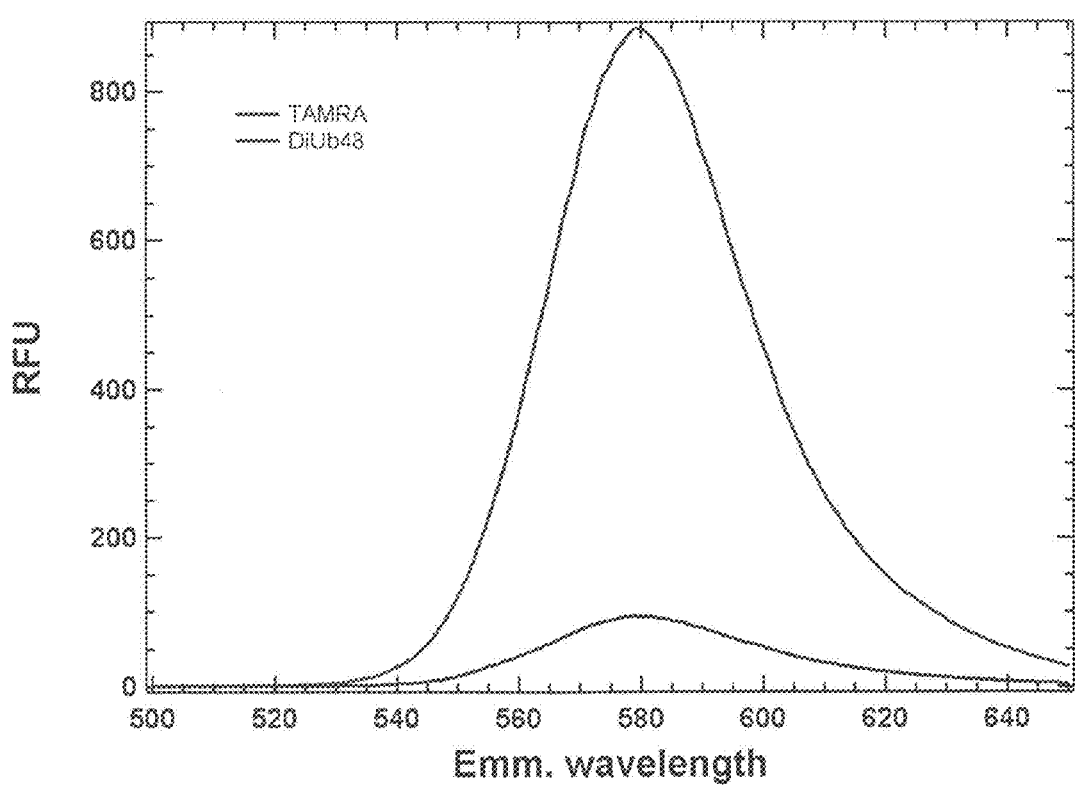
FIG. 7 shows the emission spectra of $Ub1C11_{TAMRA}$ (upper trace) and K48 linked diubiquitin $C63_{Q570}C11_{TAMRA}$ (lower trace) with an excitation wavelength of 555 nm.

FIG. 7 shows the quenching of TAMRA fluorescence by QXL™ 570 in the context of a diubiquitin molecule. The emission spectra of Ub1C11$_{TAMRA}$ (5 µM) or K48 linked diubiquitin C63$_{Q570}$C11$_{TAMRA}$ (5 µM) were measured in a Perkin-Elmer L50B spectrofluorometer using an excitation wavelength of 555 nm. The TAMRA derivatized ubiquitin monomer showed a strong fluorescence peak at 580 nm (upper trace) which was quenched by ~90% when conjugated to the QXL™570 derivatized ubiquitin.

EXAMPLE 27

Derivatization of Ubiquitin K48C, K63R, K11R with QXL™570 C2 Maleimide (Ub1Q48K63/11R)

Purified ubiquitin K48C, K63R, K11R at a concentration between 5 and 20 mg/mL in phosphate buffered saline (PBS) was mixed with QXL™570 C2 maleimide (AnaSpec, Inc., 40 mM in DMSO) at a molar ratio of 4:1, QXL™:ubiquitin. The sample was incubated at room temperature for 1 hour and the extent of modification was determined by LC-MS analysis. Typically, the reaction proceeded to >95% completion. Modified ubiquitin QXL™48, K63R, K11R was separated from free QXL™570 by chromatography on a PD10 desalting column (GEHealthcare) using PBS as the running buffer. The calculated mass of ubiquitin QXL™48, K63R, K11R is 9386.90 Da, the observed mass was 9387.54±0.1 Da. Pooled fractions from the PD10 column were concentrated to >20 mg/mL using a centrifugal concentrator (Millipore) and stored at +4° C. for use in a conjugation reaction.

EXAMPLE 28

Synthesis of K11-linked Diubiquitins from Ub1Q48K63/11R and Ub2T20

Ub1Q48K63/11R and Ub2T20 were combined in a molar ratio of 1:1.1 at a final concentration between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.6 U/ml inorganic pyrophosphatase, and 0.6 U/ml creatine phosphokinase. Conjugation was initiated by the addition of 0.5 uM Ube1 (ubiquitin activating enzyme) and 60 uM UBE2SΔC (UBE2S residues 1-195). The conjugation reaction was done at 37° C. for 24 hours. Progress of the reaction was monitored by LC-MS analysis. Every 2-3 hours 2.5 mM ATP, 0.5 uM Ube1, and 60 uM UBE2SΔC were added to the reaction. After 24 hours the reaction was diluted 10-20 fold in 50 mM Mes, pH 5.5-6 and centrifuged for 10 minutes at 4000 rpm. The diubiquitin is then separated from monomeric ubiquitins by chromatography on a strong cation exchange column in 50 mM Mes, pH 5.5-6. Monomeric ubiquitin was not retained under these conditions while salt (increased ionic strength) was required to elute the diubiquitin. The calculated mass of K11-linked diubiquitin Q48K63/11R T20 is 18,530.44 Da, the observed mass was 18,530.93±0.1 Da.

EXAMPLE 29

Verification of K11-linkage Via Digest of DiUb11Q48K63/11RT20 by AMSHcore

Figure 8:
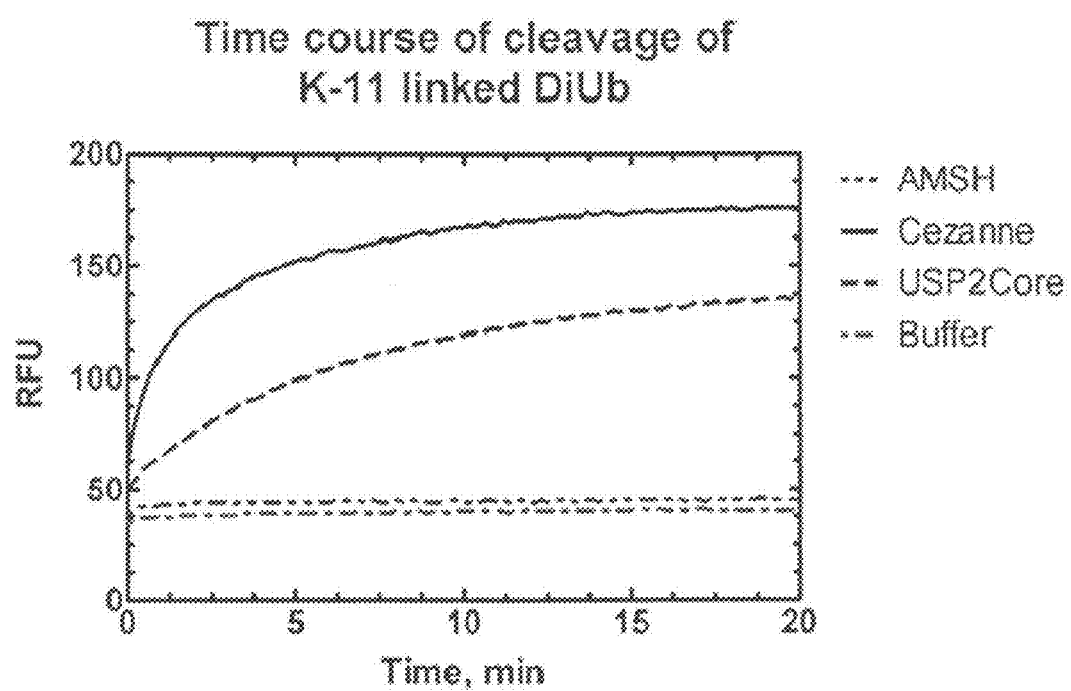
FIG. 8 shows the time course of cleavage the K11-linked DiUb Q48T20 by Cezanne, USP2Core, AMSH, or buffer alone.

The K11-linked diubiquitin Q48K63/11R T20 was incubated with 400 nM AMSHcore (a K63-linkage specific deubiquitylase) for 4 hours at 37° C. A second dose of 400 nM AMSHcore was added to the diubiquitin after the initial 1.5 hours of incubation. Any K63-linked diubiquitin Q48K63/11R T20 that formed during the conjugation will be cleaved. K11-linked diubiquitin will not be cleaved (see FIG. 8). LC-MS analysis was used to verify that the amount of K11-linked diubiquitin is the same before and after digestion by AMSHcore.

EXAMPLE 30

Cleavage of DiUbiquitins by Usp2core

The diubiquitin substrates are diluted to 1 uM with 50 mM MES pH 6.0 and adjusted to pH 8.0 with 1 M Tris-HCl pH 8.0. DTT was added to 5 mM and the diubiquitins were cleaved with 0.5 uM Usp2core. The increase in fluorescence with time was monitored by measuring the total fluorescence at 10 second intervals for 10 minutes. These data were used to determine the rates of cleavage of the substrates. Plots of time versus intensity were constructed for each substrate. Plots of wavelength versus intensity with no enzyme and following the addition of Usp2core were used to calculate the signal to background.

EXAMPLE 31

Cleavage of DiUbiquitins by Cezanne

A kinetic assay was performed to determine the cleavage of the diubiquitin substrates by Cezanne (a K11-linkage specific deubiquitylase). The substrates were diluted to 100 nM in an assay buffer consisting of 20 mM Tris-HCl, pH 7.5, 10 mM DTT, and 0.5% CHAPS. In order to quantify the extent of cleavage, a two-fold serial dilution, starting at 100 nM, of the Ub-TAMRA standard was made in the wells of a black microtiter plate. At zero time, Cezanne was added in nM quantities to the 100 nM diubiquitin substrates and the increase in fluorescence with time was monitored by measuring the total fluorescence in each well at 1 minute intervals for 60 minutes.

EXAMPLE 32

Derivatization of Ubiquitin S20C K11R with QXL570 C2 Maleimide (Ub1Q20 K11R)

Purified ubiquitin S20C, K11R at a concentration between 5 and 20 mg/mL in phosphate buffered saline (PBS) was mixed with QXL™570 C2 maleimide (AnaSpec, Inc., 40 mM in DMSO) at a molar ratio of 4:1, QXL™:ubiquitin. The sample was incubated at room temperature for 1 hour and the extent of modification was determined by LC-MS analysis. Typically, the reaction proceeded to >95% completion. Modified ubiquitin QXL™20, K11R was separated from free QXL™570 by chromatography on a PD10 desalting column (GEHealthcare) using PBS as the running buffer. The calculated mass of ubiquitin QXL™20, K11R is 9399.98 Da, the observed mass was 9400.62±0.1 Da. Pooled fractions from the PD10 column were concentrated to >20 mg/mL using a centrifugal concentrator (Millipore) and stored at +4° C. for use in a conjugation reaction.

EXAMPLE 33

Synthesis of K11-linked Diubiquitins from Ub1Q20 K11R and Ub2T20

Ub1Q20 K11R and Ub2T20 were combined in a molar ratio of 1:1.1 at a final concentration between 0.5 and 0.9 mM in a reaction buffer containing 50 mM Tris pH 8.0, 5 mM MgCl2, 0.5 mM DTT, 2.5 mM ATP, and an ATP regeneration system comprising 10 mM creatine phosphate, 0.6 U/ml inorganic pyrophosphatase, and 0.6 U/ml creatine phosphokinase. Conjugation was initiated by the addition of 0.5 uM Ube1 (ubiquitin activating enzyme) and 60 uM UBE2SΔC. The conjugation reaction was done at 37° C. for 24 hours. Progress of the reaction was monitored by LC-MS analysis. Every 2-3 hours 2.5 mM ATP, 0.5 uM Ube1, and 60 uM UBE2SΔC were added to the reaction. After 24 hours the reaction was diluted 10-20 fold in 50 mM Mes, pH 5.5-6 and centrifuged for 10 minutes at 4000 rpm. The diubiquitin was then separated from monomeric ubiquitins by chromatography on a strong cation exchange column in 50 mM Mes, pH 5.5-6. Monomeric ubiquitin was not retained under these conditions while salt (increased ionic strength) was required to elute the diubiquitin. The calculated mass of K11-linked diubiquitin Ub1Q20 K11R T20 is 18,543.52 Da, the observed mass was 18,544.28±0.1 Da.

EXAMPLE 34

Verification of K11-linkage Via Digest of DiUb11Q20K11RT20 by AMSHcore

The K11-linked diubiquitin Q20 K11R T20 was incubated with 400 nM AMSHcore for 4 hours at 37° C. A second dose of 400 nM AMSHcore was added to the diubiquitin after the initial 1.5 hours of incubation. Any K63-linked diubiquitin Q20 K11R T20 that formed during the conjugation will be cleaved. K11-linked diubiquitin will not be cleaved. LC-MS analysis is used to verify that the amount of K11-linked diubiquitin is the same before and after digestion by AMSHcore.

EXAMPLE 35

Derivatization of Ubiquitin S57C K11R with QXL™570 C2 Maleimide (Ub1Q57 K11R)

Purified ubiquitin S57C, K11R at a concentration between 5 and 20 mg/mL in phosphate buffered saline (PBS) was mixed with QXL™570 C2 maleimide (AnaSpec, Inc., 40 mM in DMSO) at a molar ratio of 4:1, QXL™:ubiquitin. The sample was incubated at room temperature for 1 hour and the extent of modification was determined by LC-MS analysis. Typically, the reaction proceeded to >95% completion. Modified ubiquitin QXL™57, K11R was separated from free QXL™570 by chromatography on a PD10 desalting column (GEHealthcare) using PBS as the running buffer. The calculated mass of ubiquitin QXL™57, K11R is 9399.98 Da, the observed mass was 9400.43±0.1 Da. Pooled fractions from the PD10 column were concentrated to >20 mg/mL using a centrifugal concentrator (Millipore) and stored at +4° C. for use in a conjugation reaction.

EXAMPLE 36

Synthesis of K11-linked Diubiquitins from Ub1Q57 K11R and Ub2T20

Ub1Q57 K11R and Ub2T20 were combined in a molar ratio of 1:1.1 at a final concentraton between 0.5 and 0.9 mM in a reaction buffer containing 50 mM Tris pH 8.0, 5 mM MgCl$_2$, 0.5 mM DTT, 2.5 mM ATP, and an ATP regeneration system comprising 10 mM creatine phosphate, 0.6 U/ml inorganic pyrophosphatase, and 0.6 U/ml creatine phosphokinase. Conjugation was initiated by the addition of 0.5 uM Ube1 (ubiquitin activating enzyme) and 60 uM UBE2SΔC. The conjugation reaction was done at 37° C. for 24 hours. Progress of the reaction was monitored by LC-MS analysis. Every 2-3 hours 2.5 mM ATP, 0.5 uM Ube1, and 60 uM UBE2SΔC were added to the reaction. After 24 hours the reaction was diluted 10-20 fold in 50 mM Mes, pH 5.5-6 and centrifuged for 10 minutes at 4000 rpm. The diubiquitin was then separated from monomeric ubiquitins by chromatography on a strong cation exchange column in 50 mM Mes, pH 5.5-6. Monomeric ubiquitin was not retained under these conditions while salt (increased ionic strength) is required to elute the diubiquitin. The calculated mass of K11-linked diubiquitin Ub1Q57 K11R T20 is 18,543.52 Da, the observed mass was 18,544.16±0.1 Da.

EXAMPLE 37

Verification of K11-linkage Via Digest of DiUb11Q57K11RT20 by AMSHcore

The K11-linked diubiquitin Q57 K11R T20 was incubated with 400 nM AMSHcore for 4 hours at 37 C. A second dose of 400 nM AMSHcore was added to the diubiquitin after the initial 1.5 hours of incubation. Any K63-linked diubiquitin Q57 K11R T20 that formed during the conjugation will be cleaved. K11-linked diubiquitin will not be cleaved. LC-MS analysis is used to verify that the amount of K11-linked diubiquitin is the same before and after digestion by AMSHcore.

EXAMPLE 38

Derivatization of Ubiquitin K63C K11R with QXL570 C2 Maleimide (Ub1Q63 K11R)

Purified ubiquitin K63C, K11R at a concentration between 5 and 20 mg/mL in phosphate buffered saline (PBS) was mixed with QXL™570 C2 maleimide (AnaSpec, Inc., 40 mM in DMSO) at a molar ratio of 4:1, QXL™:ubiquitin. The sample was incubated at room temperature for 1 hr and the extent of modification was determined by LC-MS analysis. Typically, the reaction proceeded to >95% completion. Modified ubiquitin QXL™63, K11R was separated from free QXL™570 by chromatography on a PD10 desalting column (GEHealthcare) using PBS as the running buffer. The calculated mass of ubiquitin QXL™63, K11R is 9358.88 Da, the observed mass was 9359.70±0.1 Da. Pooled fractions from the PD10 column were concentrated to >20 mg/mL using a centrifugal concentrator (Millipore) and stored at +4° C. for use in a conjugation reaction.

EXAMPLE 39

Synthesis of K11-linked Diubiquitins from Ub1Q63 K11R and Ub2T20

Ub1Q63 K11R and Ub2T20 are combined in a molar ratio of 1:1.1 at a final concentraton between 0.5 and 0.9 mM in a reaction buffer containing 50 mM Tris pH 8.0, 5 mM MgCl2, 0.5 mM DTT, 2.5 mM ATP, and an ATP regeneration system comprising 10 mM creatine phosphate, 0.6 U/ml inorganic pyrophosphatase, and 0.6 U/ml creatine phosphokinase. Conjugation was initiated by the addition of 0.5 uM Ube1 (ubiquitin activating enzyme) and 60 uM UBE2SΔC. The conjugation reaction was done at 37° C. for 24 hours. Progress of the reaction was monitored by LC-MS analysis. Every 2-3 hours 2.5 mM ATP, 0.5 uM Ube1, and 60 uM UBE2SΔC were added to the reaction. After 24 hours the reaction was diluted 10-20 fold in 50 mM Mes, pH 5.5-6 and centrifuged for 10 minutes at 4000 rpm. The diubiquitin was then separated from monomeric ubiquitins by chromatography on a strong cation exchange column in 50 mM Mes, pH 5.5-6. Monomeric ubiquitin was not retained under these conditions while salt (increased ionic strength) is required to elute the diubiquitin. The calculated mass of K11-linked diubiquitin Ub1Q63 K11R T20 is 18,502.42 Da, the observed mass was 18,503.23+0.1 Da.

EXAMPLE 40

Verification of K11-linkage Via Digest of DiUb11Q63K11RT20 by AMSHcore

The K11-linked diubiquitin Q63 K11R T20 was incubated with 400 nM AMSHcore for 4 hours at 37 C. A second dose of 400 nM AMSHcore was added to the diubiquitin after the initial 1.5 hours of incubation. Any K63-linked diubiquitin Q63 K11R T20 that formed during the conjugation will be cleaved. K11-linked diubiquitin will not be cleaved. LC-MS analysis was used to verify that the amount of K11-linked diubiquitin is the same before and after digestion by AMSHcore.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A substrate for measuring the isopeptidase activity of a deubiquitinase comprising:
   A) a first ubiquitin or ubiquitin-like (Ubl) molecule operably linked to at least one first energy transfer pair member; and
   B) a second ubiquitin or ubiquitin-like (Ubl) molecule operably linked to at least one second energy transfer pair member;
   wherein said first ubiquitin or ubiquitin-like (Ubl) molecule is operably linked to said ubiquitin or ubiquitin-like (Ubl) molecule by an isopeptide bond from the C-terminus of said first ubiquitin or ubiquitin-like (Ubl) molecule to the side chain of a lysine residue of said second ubiquitin or ubiquitin-like (Ubl) molecule,
   wherein said ubiquitin-like (Ubl) molecule is selected from the group consisting of small ubiquitin like-modifier-1 (SUMO), SUMO-2, SUMO-3, SUMO-4, ISG-15, homologous to ubiquitin 1 (HUB1), autophagy-defective 12 (APG12), ubiquitin-related modifier 1 (URM1), NEDD8, FAT10, and APG8,
   wherein said first and second energy transfer pair members are individually either a fluorescent group or a quenching group,
   wherein said first and second ubiquitin or ubiquitin-like (Ubl) molecules comprise a cysteine residue introduced at a position corresponding to amino acid residues at positions between 8 and 70 of the amino acid sequence of SEQ ID NO: 1,
   wherein said first and second energy transfer pair members are attached to said first and second ubiquitin or ubiquitin-like (Ubl) molecules at the introduced cysteine residues, and wherein said substrate further comprises at least one additional ubiquitin or ubiquitin-like (Ubl) molecule linked to said first or second ubiquitin or ubiquitin-like (Ubl) molecule.

2. The substrate of claim 1, wherein said first and second ubiquitin or ubiquitin-like (Ubl) molecules comprises an amino acid sequence having at least 95% sequence identity to the amino acid sequence of SEQ ID NO: 1.

3. The substrate of claim 1, wherein said first energy transfer pair member is a fluorescent group and said second energy transfer pair member is a quenching group.

4. The substrate of claim 1, wherein said second energy transfer pair member is a fluorescent group and said first energy transfer pair member is a quenching group.

5. The substrate of claim 1, wherein said first and second ubiquitin or ubiquitin-like (Ubl) molecules are ubiquitin.

6. The substrate of claim 5, wherein said cysteine residue is introduced at a position corresponding to amino acid residues at position 11, 20, 31, 34, 48, 57, or 63 of the amino acid sequence of SEQ ID NO: 1.

7. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 6 of the amino acid sequence of SEQ ID NO: 1.

8. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 11 of the amino acid sequence of SEQ ID NO: 1.

9. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 27 of the amino acid sequence of SEQ ID NO: 1.

10. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 29 of the amino acid sequence of SEQ ID NO: 1.

11. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 33 of the amino acid sequence of SEQ ID NO: 1.

12. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 48 of the amino acid sequence of SEQ ID NO: 1.

13. The substrate of claim 1, wherein said first and second ubiquitin or ubiquitin-like (Ubl) molecules are ubiquitin and wherein said isopeptide bond is between the C-terminus of said first ubiquitin and the lysine of said second ubiquitin corresponding to amino acid residue at position 63 of the amino acid sequence of SEQ ID NO: 1.

14. A method of synthesizing the substrate of claim 1, said method comprising joining said first and second ubiquitin or ubiquitin-like (Ubl) molecules by intein-based thioester chemistry.

15. A method of synthesizing the substrate of claim 1, said method comprising joining said first and second ubiquitin or ubiquitin-like (Ubl) molecules enzymatically with at least one enzyme.

16. The method of claim 15, wherein said enzymes comprise an E1 ubiquitin activating enzyme, an E2 ubiquitin conjugating enzyme, and an ATP regeneration system.

17. The method of claim 15, wherein said enzymes comprise an Ube1 ubiquitin activating enzyme, an E2 ubiquitin conjugating enzyme, and an ATP regeneration system.

18. The method of claim 15, wherein said enzymes comprise an E1 ubiquitin activating enzyme, the UBE2 K ubiquitin conjugating enzyme, and an ATP regeneration system.

19. The method of claim 15, wherein said enzymes comprise an E1 ubiquitin activating enzyme, the Ubc13/MMS2 ubiquitin conjugating enzyme complex, and an ATP regeneration system.

20. The method of claim 15, wherein said enzymes comprise an E1 ubiquitin activating enzyme, a Lys6 specific E2 ubiquitin conjugating enzyme, and an ATP regeneration system.

21. The method of claim 15, wherein said enzymes comprise an E1 ubiquitin activating enzyme, the UBE2 S ubiquitin conjugating enzyme, and an ATP regeneration system.

22. The method of claim 15, wherein said enzymes comprise an E1 ubiquitin activating enzyme, a Lys27 specific E2 ubiquitin conjugating enzyme, and an ATP regeneration system.

23. The method of claim 15, wherein said enzymes comprise an E1 ubiquitin activating enzyme, a Lys29 specific E2 ubiquitin conjugating enzyme, and an ATP regeneration system.

24. The method of claim 15, wherein said enzymes comprise an E1 ubiquitin activating enzyme, a Lys33 specific E2 ubiquitin conjugating enzyme, and an ATP regeneration system.

25. The substrate of claim 1, wherein said quenching group is selected from the group consisting of QXL™490, QXL™570, tetramethylaminorhodamine (TAMRA), 4-[{4-(dimethylamino)phenyl}azo]benzoic acid (DABCYL), TIDE Quencher™, and Black Hole Quencher™2.

26. The substrate of claim 1, wherein said fluorescent group is selected from the group consisting of tetramethylaminorhodamine (TAMRA), fluorescein, or 5-[(2-aminoethyl)amino]naphthalene-1-sulfonic acid (EDANS).

27. A method for detecting an isopeptidase activity in a sample comprising contacting said sample with the substrate of claim 1, and detecting fluorescence in said sample, wherein a change in said fluorescence is indicative of isopeptidase activity.

28. A method for screening for agents capable of modulating the activity of an isopeptidase in a sample comprising:
   A) contacting the isopeptidase with the substrate of claim 1 in the presence of a test agent; and
   B) detecting fluorescence in said sample,
   wherein a difference in the level of fluorescence in the presence of said test agent as compared to the absence of said test agent indicates that said agent modulates the activity of the isopeptidase.

29. A kit for detecting isopeptidase activity, comprising at least one substrate of claim 1 and, optionally, at least one item from the group consisting of:
   A) at least one fluorophore labeled control,
   B) instructions, and
   C) at least one buffer.

30. The kit of claim 29, wherein said substrates are contained within a microassay plate.

31. The substrate of claim 1, wherein said additional ubiquitin or ubiquitin-like (Ubl) molecules are wild-type ubiquitin or ubiquitin-like (Ubl) molecules.

32. The substrate of claim 1, wherein said substrate comprises at least four ubiquitin or ubiquitin-like (Ubl) molecules.

33. The substrate of claim 1, wherein said second ubiquitin or ubiquitin-like (Ubl) molecule comprises a fluorophore at its C-terminus, wherein said fluorophore does not interact with said energy transfer pair.

34. A microarray comprising at least one substrate of claim 1.

35. The method of claim 28, wherein said screening is a high throughput screening.

* * * * *

SEQUENCE LISTING

```
<160> NUMBER OF SEQ ID NOS: 1

<210> SEQ ID NO 1
<211> LENGTH: 76
<212> TYPE: PRT
<213> ORGANISM: Homo Sapiens

<400> SEQUENCE: 1

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75
```